United States Patent
Hopper et al.

(10) Patent No.: US 11,559,241 B2
(45) Date of Patent: Jan. 24, 2023

(54) METHODS AND SYSTEMS FOR REDUCING FALSE DECLARATIONS OF ARRHYTHMIAS

(71) Applicant: Pacesetter, Inc., Sylmar, CA (US)

(72) Inventors: Donald Hopper, Maple Grove, MI (US); Luke C. McSpadden, Los Angeles, CA (US); Fujian Qu, San Jose, CA (US); Gene Bornzin, Sylmar, CA (US); Sinny Delacroix, Sylmar, CA (US)

(73) Assignee: Pacesetter, Inc., Sylmar, CA (US)

( * ) Notice: Subject to any disclaimer, the term of this patent is extended or adjusted under 35 U.S.C. 154(b) by 639 days.

(21) Appl. No.: 16/589,978

(22) Filed: Oct. 1, 2019

(65) Prior Publication Data

US 2021/0093215 A1    Apr. 1, 2021

(51) Int. Cl.
| | |
|---|---|
| *A61B 5/352* | (2021.01) |
| *A61B 5/00* | (2006.01) |
| *A61B 5/316* | (2021.01) |
| *A61B 5/349* | (2021.01) |
| *A61B 5/363* | (2021.01) |
| *A61B 5/113* | (2006.01) |

(52) U.S. Cl.
CPC ............... *A61B 5/352* (2021.01); *A61B 5/316* (2021.01); *A61B 5/349* (2021.01); *A61B 5/363* (2021.01); *A61B 5/686* (2013.01); *A61B 5/721* (2013.01); *A61B 5/113* (2013.01)

(58) Field of Classification Search
CPC ......... A61B 5/352; A61B 5/316; A61B 5/349; A61B 5/363; A61B 5/721; A61B 5/113
See application file for complete search history.

(56) References Cited

U.S. PATENT DOCUMENTS

| | | |
|---|---|---|
| 5,090,418 A | 2/1992 | Squires et al. |
| 5,630,834 A | 5/1997 | Bardy |
| 5,987,352 A | 11/1999 | Klein et al. |
| 6,115,628 A | 9/2000 | Stadler et al. |
| 6,115,630 A | 9/2000 | Stadler et al. |
| 6,128,526 A | 10/2000 | Stadler et al. |
| 6,324,421 B1 | 11/2001 | Stadler et al. |
| 6,381,493 B1 | 4/2002 | Stadler et al. |
| 6,397,100 B2 | 5/2002 | Stadler et al. |

(Continued)

*Primary Examiner* — Catherine M Voorhees
(74) *Attorney, Agent, or Firm* — The Small Patent Law Group LLC; Dean D. Small

(57) ABSTRACT

Computer implemented methods and systems are provided that comprise, under control of one or more processors of a medical device, where the one or more processors are configured with specific executable instructions. The methods and systems obtain motion data indicative of at least one of a posture or a respiration cycle; obtain cardiac activity (CA) signals for a series of beats; identify whether a characteristic of interest (COI) from at least a first segment of the CA signals exceeds a COI limit; analyze the motion data to determine whether at least one of the posture or respiration cycle at least in part caused the COI to exceed the COI limit. Based on the analyzing operation, the methods and systems automatically adjust a CA sensing parameter utilized by the medical device to detect R-waves in subsequent CA signals; and detect an arrhythmia based on a presence or absence of one or more of the R-waves in at least a second segment of the CA signals.

16 Claims, 14 Drawing Sheets

(56) References Cited

U.S. PATENT DOCUMENTS

| | | | |
|---|---|---|---|
| 6,412,490 B1 | 7/2002 | Lee | |
| 6,438,409 B1 | 8/2002 | Malik et al. | |
| 6,496,715 B1 | 12/2002 | Lee et al. | |
| 6,595,927 B2 | 7/2003 | Pitts-Crick et al. | |
| 6,752,765 B1 | 6/2004 | Jensen et al. | |
| 6,937,899 B2 | 8/2005 | Sheldon et al. | |
| 6,964,641 B2 | 11/2005 | Cho et al. | |
| 7,027,858 B2 | 4/2006 | Cao et al. | |
| 7,133,718 B2 | 11/2006 | Bakken et al. | |
| 7,167,747 B2 | 1/2007 | Gunderson et al. | |
| 7,181,268 B2 | 2/2007 | Sheldon et al. | |
| 7,181,269 B1 | 2/2007 | Kroll | |
| 7,254,440 B1 | 8/2007 | Kroll | |
| 7,266,409 B2 | 9/2007 | Gunderson | |
| 7,333,855 B2 | 2/2008 | Gunderson et al. | |
| 7,369,893 B2 | 5/2008 | Gunderson | |
| 7,403,813 B1 | 7/2008 | Farazi et al. | |
| 7,447,540 B1 | 11/2008 | Nabutovsky et al. | |
| 7,496,409 B2 | 2/2009 | Greenhut et al. | |
| 7,734,333 B2 | 6/2010 | Ghanem | |
| 7,734,336 B2 | 6/2010 | Ghanem et al. | |
| 7,742,812 B2 | 6/2010 | Ghanem et al. | |
| 7,756,571 B1 | 7/2010 | Farazi | |
| 7,761,142 B2 | 7/2010 | Ghanem et al. | |
| 7,761,150 B2 | 7/2010 | Ghanem et al. | |
| 7,769,452 B2 | 8/2010 | Ghanem et al. | |
| 7,774,049 B2 | 8/2010 | Ghanem et al. | |
| 7,813,791 B1 | 10/2010 | Gill et al. | |
| 7,881,792 B1 | 2/2011 | Farazi | |
| 7,894,894 B2 | 2/2011 | Stadler et al. | |
| 7,904,153 B2 | 3/2011 | Greenhut et al. | |
| 7,907,993 B2 | 3/2011 | Ghanem et al. | |
| 7,909,764 B1 | 3/2011 | Wenzel et al. | |
| 7,937,135 B2 | 5/2011 | Ghanem et al. | |
| 7,941,214 B2 | 5/2011 | Kleckner et al. | |
| 7,953,488 B2 | 5/2011 | Casavant et al. | |
| 7,970,473 B2 | 6/2011 | Nabutovsky et al. | |
| 7,974,690 B2 | 7/2011 | Kracker | |
| 7,986,994 B2 | 7/2011 | Stadler et al. | |
| 7,991,471 B2 | 8/2011 | Ghanem et al. | |
| 7,996,070 B2 | 8/2011 | van Dam et al. | |
| 8,005,539 B2 | 8/2011 | Burnes et al. | |
| 8,032,206 B1 * | 10/2011 | Farazi | A61B 5/318 |
| | | | 600/521 |
| 8,050,751 B2 | 11/2011 | Zhang et al. | |
| 8,060,198 B2 | 11/2011 | Lian et al. | |
| 8,068,901 B2 | 11/2011 | Ghanem et al. | |
| 8,078,277 B2 | 12/2011 | Gunderson et al. | |
| 8,095,206 B2 | 1/2012 | Ghanem et al. | |
| 8,116,873 B2 | 2/2012 | Anderson et al. | |
| 8,126,553 B2 | 2/2012 | Mayotte | |
| 8,160,684 B2 | 4/2012 | Ghanem et al. | |
| 8,200,322 B2 | 6/2012 | Ousdigian et al. | |
| 8,204,590 B2 | 6/2012 | Sambelashvili et al. | |
| 8,249,708 B2 | 8/2012 | Krause et al. | |
| 8,255,046 B2 | 8/2012 | Sarkar et al. | |
| 8,260,412 B2 | 9/2012 | Krause et al. | |
| 8,260,419 B2 | 9/2012 | Gunderson | |
| 8,265,771 B2 | 9/2012 | Donofrio et al. | |
| 8,271,072 B2 | 9/2012 | Houben et al. | |
| 8,301,233 B2 | 10/2012 | Zhang et al. | |
| 8,301,263 B2 | 10/2012 | Donofrio et al. | |
| 8,306,618 B2 | 11/2012 | Ghanem et al. | |
| 8,321,003 B2 | 11/2012 | Zhang et al. | |
| 8,374,692 B2 | 2/2013 | Bobgan et al. | |
| 8,396,543 B2 | 3/2013 | Hoeppner et al. | |
| 8,406,893 B2 | 3/2013 | Krause et al. | |
| 8,428,718 B2 | 4/2013 | Stadler et al. | |
| 8,433,402 B2 | 4/2013 | Ruben et al. | |
| 8,433,409 B2 | 4/2013 | Johnson et al. | |
| 8,435,185 B2 | 5/2013 | Ghanem et al. | |
| 8,435,186 B2 | 5/2013 | Hettrick et al. | |
| 8,442,627 B2 | 5/2013 | Hess | |
| 8,452,394 B2 | 5/2013 | Burnes et al. | |
| 8,463,384 B2 | 6/2013 | Germanson et al. | |
| 8,473,057 B2 | 6/2013 | Donofrio et al. | |
| 8,494,649 B2 | 7/2013 | Stancer et al. | |
| 8,513,120 B2 | 8/2013 | Fleischhauer | |
| 8,521,293 B2 | 8/2013 | Anderson et al. | |
| 8,527,045 B2 | 9/2013 | Krause et al. | |
| 8,532,769 B2 | 9/2013 | Kornet et al. | |
| 8,532,779 B2 | 9/2013 | Krause et al. | |
| 8,571,664 B2 | 10/2013 | Anderson et al. | |
| 8,571,682 B2 | 10/2013 | Arisso et al. | |
| 8,577,457 B2 | 11/2013 | Miller et al. | |
| 8,583,233 B2 | 11/2013 | Betzoid | |
| 8,606,355 B1 | 12/2013 | Krause | |
| 8,611,996 B2 | 12/2013 | Donofrio et al. | |
| 8,626,278 B2 | 1/2014 | Park et al. | |
| 8,644,931 B2 | 2/2014 | Stadler et al. | |
| 8,649,864 B2 | 2/2014 | Hastings et al. | |
| 8,660,643 B2 | 2/2014 | Gunderson | |
| 8,682,436 B2 | 3/2014 | Ghosh et al. | |
| 8,688,210 B2 | 4/2014 | Burnes et al. | |
| 8,718,769 B2 | 5/2014 | Hilpish et al. | |
| 8,751,000 B2 | 6/2014 | Miller et al. | |
| 8,755,881 B2 | 6/2014 | Kaiser et al. | |
| 8,761,886 B2 | 6/2014 | Stancer et al. | |
| 8,774,918 B2 | 6/2014 | Donofrio et al. | |
| 8,781,585 B2 | 7/2014 | Gunderson et al. | |
| 8,798,750 B2 | 8/2014 | Gunderson et al. | |
| 8,798,751 B2 | 8/2014 | Spear et al. | |
| 8,831,713 B2 | 9/2014 | Stadler et al. | |
| 8,849,385 B2 | 9/2014 | Kracker | |
| 8,855,755 B2 | 10/2014 | Zhang et al. | |
| 8,886,307 B2 | 11/2014 | Sambelashvili et al. | |
| 8,886,315 B2 | 11/2014 | Ghosh | |
| 8,954,138 B2 | 2/2015 | Maskara et al. | |
| 8,965,507 B2 | 2/2015 | Mahajan et al. | |
| 8,996,111 B2 | 3/2015 | Marshall et al. | |
| 9,026,201 B2 | 5/2015 | Zhang et al. | |
| 9,026,206 B2 | 5/2015 | Krause et al. | |
| 9,026,208 B2 | 5/2015 | Morley et al. | |
| 9,037,240 B2 | 5/2015 | Gunderson | |
| 9,077,030 B2 | 7/2015 | Norton et al. | |
| 9,079,037 B2 | 7/2015 | Martinez et al. | |
| 9,101,281 B2 | 8/2015 | Reinert et al. | |
| 9,174,062 B2 | 11/2015 | Stadler et al. | |
| 9,192,769 B2 | 11/2015 | Donofrio et al. | |
| 9,232,898 B2 | 1/2016 | Spear et al. | |
| 9,289,613 B2 | 3/2016 | Burnes et al. | |
| 9,352,165 B2 | 5/2016 | Zhang | |
| 9,364,162 B2 | 6/2016 | Cao et al. | |
| 9,375,181 B2 | 6/2016 | Hemming et al. | |
| 9,403,019 B2 | 8/2016 | Sambelashvili et al. | |
| 9,408,574 B2 | 8/2016 | Stadler et al. | |
| 9,414,757 B2 | 8/2016 | Hopenfeld | |
| 9,451,905 B2 | 9/2016 | Op Den Buijs et al. | |
| 9,486,766 B2 | 10/2016 | Sheldon et al. | |
| 9,522,271 B2 | 12/2016 | Arcot-Krishnamurthy et al. | |
| 9,522,277 B2 | 12/2016 | Gunderson | |
| 9,526,908 B2 | 12/2016 | Zhang et al. | |
| 9,539,428 B2 | 1/2017 | Germanson et al. | |
| 9,558,336 B2 | 1/2017 | Lee | |
| 9,559,353 B2 | 1/2017 | Norton et al. | |
| 9,561,005 B2 | 2/2017 | Zhang | |
| 9,561,377 B2 | 2/2017 | Gunderson | |
| 9,566,012 B2 | 2/2017 | Greenhut et al. | |
| 9,592,392 B2 | 3/2017 | Demmer et al. | |
| 9,597,505 B2 | 3/2017 | Donofrio et al. | |
| 9,597,513 B2 | 3/2017 | Sheldon et al. | |
| 9,597,525 B2 | 3/2017 | Cao et al. | |
| 9,610,025 B2 | 4/2017 | Zhang | |
| 9,636,506 B2 | 5/2017 | Gunderson | |
| 9,649,498 B2 | 5/2017 | Mahajan et al. | |
| 9,662,073 B2 | 5/2017 | Zhang et al. | |
| 9,750,932 B2 | 9/2017 | Spear et al. | |
| 9,775,559 B2 | 10/2017 | Zhang et al. | |
| 9,775,987 B2 | 10/2017 | Donofrio et al. | |
| 9,795,312 B2 | 10/2017 | Greenhut et al. | |
| 9,808,640 B2 | 11/2017 | Zhang | |
| 9,814,886 B2 | 11/2017 | Zhou et al. | |
| 9,848,778 B2 | 12/2017 | Soykan et al. | |
| 9,872,630 B2 | 1/2018 | Stadler et al. | |

(56) References Cited

U.S. PATENT DOCUMENTS

| | | | |
|---|---|---|---|
| 9,895,080 B2 | 2/2018 | Stadler et al. | |
| 9,907,962 B2 | 3/2018 | Kornet et al. | |
| 9,924,885 B2 | 3/2018 | Stadler et al. | |
| 9,950,155 B2 | 4/2018 | Gunderson et al. | |
| 9,956,423 B2 | 5/2018 | Zhang et al. | |
| 9,974,964 B2 | 5/2018 | Martinez et al. | |
| 10,065,045 B2 | 9/2018 | Zhang | |
| 10,118,042 B2 | 11/2018 | Gunderson et al. | |
| 10,124,179 B2 | 11/2018 | Norton et al. | |
| 10,143,847 B1 | 12/2018 | Edmonson et al. | |
| 11,400,303 B2 * | 8/2022 | Kim | A61B 5/1123 |
| 2013/0096445 A1 * | 4/2013 | Patel | A61B 5/7264 |
| | | | 600/509 |
| 2014/0275832 A1 * | 9/2014 | Muehlsteff | A61B 5/6889 |
| | | | 600/301 |
| 2018/0220917 A1 * | 8/2018 | Brisben | A61B 5/4836 |
| 2020/0376284 A1 * | 12/2020 | Gill | A61B 5/686 |

\* cited by examiner

METHODS AND SYSTEMS FOR REDUCING FALSE DECLARATIONS OF ARRHYTHMIAS

BACKGROUND

Embodiments herein generally relate to methods and systems for reducing false declarations of arrhythmias, and more particularly, to methods and systems for reducing false declarations of arrhythmias due to undersensing or oversensing R-waves.

Implantable medical devices (IMDs) are well known in the art. IMDs may take the form of implantable defibrillators or cardioverters which treat accelerated rhythms of the heart such as fibrillation. IMDs may also take the form of implantable pacemakers which maintains the heart rate above a prescribed limit, such as, for example, to treat a bradycardia. IMDs may also incorporate more than one of a pacemaker, a cardioverter and a defibrillator. Defibrillators may include "shock only" functionality or, in addition to shocking functionality, a defibrillator may be capable of providing cardiac resynchronization therapy (CRT) functionality.

IMDs are coupled to one or more leads that include electrodes to sense one or more types of information and to deliver various types of treatments and/or therapies. IMDs typically include various sensing circuitry and logic that monitor a heart for cardiac activity signals, and analyze the cardiac activity signals to identify normal sinus rhythm, arrhythmias, physiological status of the patient, and the like. IMDs may be configured to generate alerts and/or deliver therapies based on the identification of cardiac events (e.g., arrhythmias), physiological status of the patient, and the like. However, IMDs may incorrectly interpret the cardiac activity signals and declare a false cardiac event and/or physiological status of the patient due to oversensing or undersensing one or more characteristics of interest of the cardiac activity signals. For example, adequate detection of atrial contraction (e.g., P-waves, the QRS complex, R-wave amplitude, and the like) is important for reliable cardiac event (e.g., arrhythmia) detection and/or treatment delivery. Conventionally, a clinician may adjust certain programmable parameters of the sensing circuitry during implantation or revision of the IMD to change the fixed sensitivity of the sensing circuit in order to ensure more accurate detection of one or more characteristics of interest of the cardiac activity signals. One consideration for achieving adequate detection of the cardiac activity signals is placement of the IMD in an optimal anatomical orientation and/or location. However, it may not be possible to always achieve the optimal anatomical location and/or orientation during implantation. Furthermore, other factors such as patient posture and a respiration cycle may impact the ability of the IMD to correctly detect and interpret the cardiac activity signals post-implantation.

Oversensing or undersensing of one or more characteristics of interest (e.g., R-waves) of cardiac activity signals may adversely impact patient outcomes by leading to false declarations of cardiac events. For example, therapies and/or interventions delivered by IMDs with defibrillation functionality are painful. When defibrillation therapies and/or interventions are unnecessarily administered, they have a deleterious impact on quality of life. Unnecessary administration of defibrillation therapies and/or interventions occur at a rate that renders them a concern in the long-term management of the corresponding patient population. Accordingly, a desire remains for methods and systems to reduce false declaration of cardiac events due to undersensing or oversensing of R-waves.

SUMMARY

In accordance with embodiments herein, a computer implemented method is provided that comprises, under control of one or more processors of a medical device, where the one or more processors are configured with specific executable instructions, obtaining motion data indicative of at least one of a posture or a respiration cycle; obtaining cardiac activity (CA) signals for a series of beats; identifying whether a characteristic of interest (COI) from at least a first segment of the CA signals exceeds a COI limit; analyzing the motion data to determine whether at least one of the posture or respiration cycle at least in part caused the COI to exceed the COI limit; based on the analyzing operation, automatically adjusting a CA sensing parameter utilized by the medical device to detect R-waves in subsequent CA signals; and detecting an arrhythmia based on a presence or absence of one or more of the R-waves in at least a second segment of the CA signals.

Optionally, the CA sensing parameter defines a sensitivity profile and wherein the adjusting operation further comprises adjusting the CA sensing parameter to change a sensitivity of the sensitivity profile to at least reduce false arrhythmia detection due to undersensing or oversensing R-waves. Optionally, the detecting operation further comprises detecting the absence of one or more of the R-waves in at least the second segment of the CA signals and based thereon declaring a brady pause arrhythmia. Optionally, the identifying, analyzing, adjusting and detecting operations are performed at least one of: i) beat by beat, or ii) for ensembles of beats. Optionally, the COI limit represents at least one of an expected variability of an amplitude of an R-wave or a presence of the R-wave. Optionally, the analyzing operation further comprises comparing the motion data to baseline motion data, wherein the baseline motion data is indicative of at least one of a supine baseline posture or a baseline respiration cycle, the comparing operation identifying motion changes that are associated with changes in an amplitude of the CA signals that occur with different postures and minute ventilation increase and decrease changes.

Optionally, the motion data is indicative of the posture, the determining operation further comprises determining that the motion data is indicative of a posture change that reduced an amplitude of the CA signals by an amount sufficient to cause the COI to exceed the COI limit. Optionally, the determining operation further comprises determining that the posture change is a type of posture change that reduces an amplitude of R-waves in the CA signals by an amount sufficient to prevent detection based on a sensing profile, wherein the CA sensing parameters are adjusted automatically to adjust the sensing profile. Optionally, the motion data is indicative of the respiration cycle, the determining operation further comprises determining that the respiration cycle reduced an amplitude of the CA signals. Optionally, the method further comprises comparing the subsequent CA signals to a current sensitivity level to determine whether one or more R-waves are present within the subsequent CA signals. Optionally, the method repeats the comparing operation while progressively adjusting the current sensitivity level until i) the one or more R-waves are detected in a beat segment of interest in the CA signals and/or ii) the current sensitivity level reaches a sensitivity limit.

In accordance with embodiments a system is provided that comprises: one or more processors; and a memory coupled to the one or more processors, wherein the memory stores program instructions, wherein the program instructions are executable by the one or more processors to: obtain motion data indicative of at least one of a posture or a respiration cycle; obtain cardiac activity (CA) signals for a series of beats; identify whether a characteristic of interest (COI) from at least a first segment of the CA signals exceeds a COI limit; analyze the motion data to determine whether at least one of the posture or respiration cycle at least in part caused the COI to exceed the COI limit; based on the analyze operation, automatically adjust a CA sensing parameter utilized by the medical device to detect R-waves in subsequent CA signals; and detect an arrhythmia based on a presence or absence of one or more of the R-waves in at least a second segment of the CA signals.

Optionally, the CA sensing parameter defines a sensitivity profile and wherein the adjust includes adjust the CA sensing parameter to change a sensitivity of the sensitivity profile to at least reduce false arrhythmia detection due to undersensing or oversensing R-waves. Optionally, the detection operation includes detect the absence of one or more of the R-waves in at least the second segment of the CA signals and based thereon declare a brady pause arrhythmia. Optionally, the program instructions are further executable by the one or more processors to perform the identify, analyze, adjust and detect on at least one of: i) beat by beat, or ii) for ensembles of beats. Optionally, the COI limit represents at least one of an expected variability of an amplitude of an R-wave or a presence of the R-wave. Optionally, the analysis includes compare the motion data to baseline motion data, wherein the baseline motion data is indicative of at least one of a supine baseline posture or a baseline respiration cycle, the compare identifying motion changes that are associated with changes in an amplitude of the CA signals that occur with different postures and minute ventilation increase and decrease changes.

Optionally, the motion data is indicative of the posture, the determine includes determine that the motion data is indicative of a posture change that reduced an amplitude of the CA signals by an amount sufficient to cause the COI to exceed the COI limit. Optionally, the determination includes determine that the posture change is a type of posture change that reduces an amplitude of R-waves in the CA signals by an amount sufficient to prevent detection based on a sensing profile and, wherein the program instructions are further executable by the one or more processors to automatically adjust the CA sensing parameters to adjust the sensing profile. Optionally, the motion data is indicative of the respiration cycle, the determine includes determine that the respiration cycle reduced an amplitude of the CA signals.

DETAILED DESCRIPTION

Figure 1:
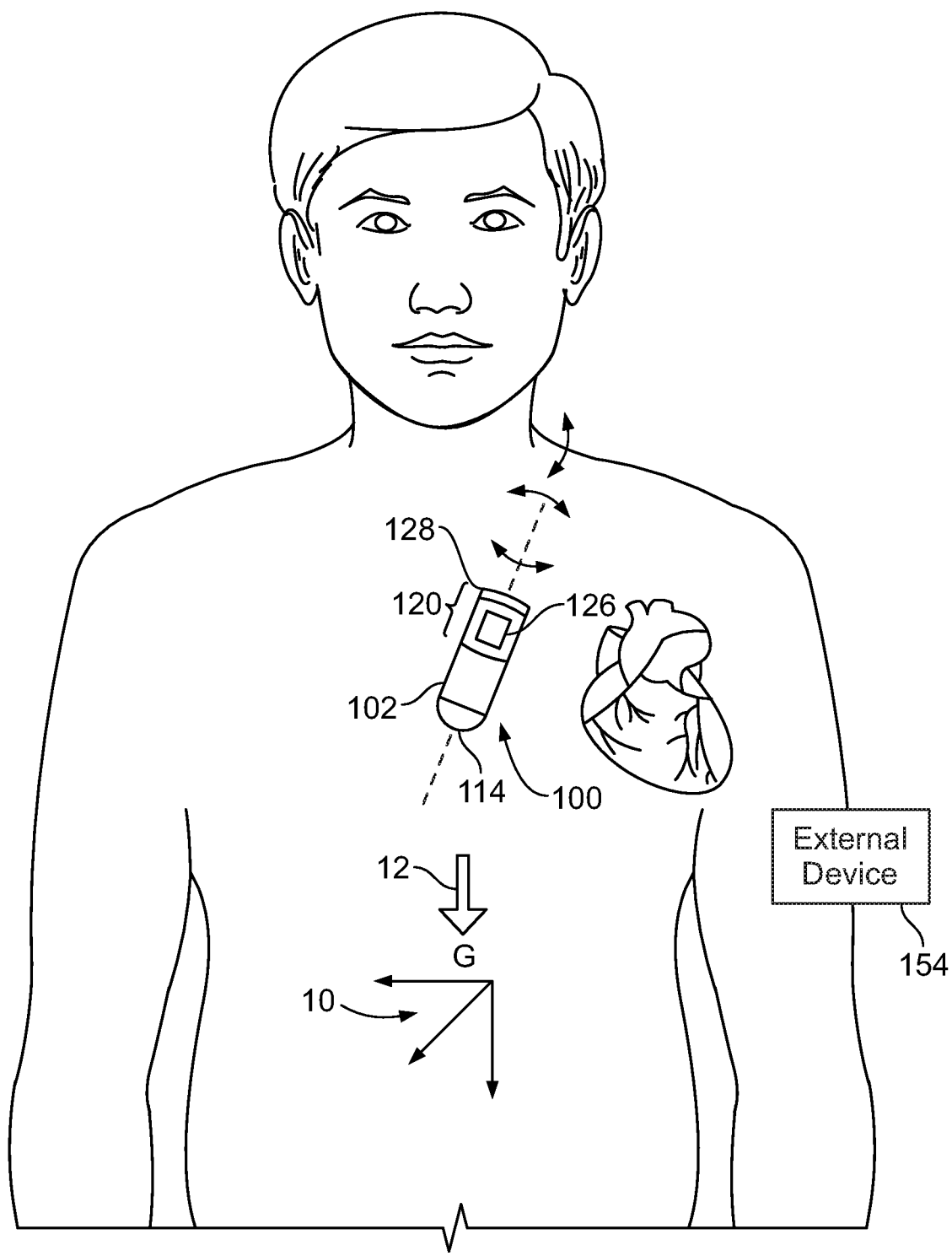
FIG. 1 illustrates a graphical representation of a heart with an implantable medical device (IMD) for reducing false declarations of cardiac events due to undersensing or oversensing of R-waves in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation.

The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

All references, including publications, patent applications and patents, cited herein are hereby incorporated by reference to the same extent as if each reference were individually and specifically indicated to be incorporated by reference and were set forth in its entirety herein.

Terms

The terms "posture" and "patient posture" refer to postural states and/or activity levels of a patient including supine, laying on a right side, laying on a left side, sitting, standing, isometric arm exercises (e.g., pushing, pulling, and the like), ballottement, chest thump, device pressure (e.g., top, mid, and base), arm flap, hand shake, and the like.

The term "activity level" refers to types of activity currently experienced by a patient, including stationary state, rest state, exercise state, walking state, and the like.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes and/or by electrodes positioned within or proximate to the heart wall and/or chambers of the heart.

The phrases "arrhythmia treatment", "in connection with treating a heart condition" and similar phrases, as used herein include, but are not limited to, delivering an electrical stimulation or drug therapy to a heart condition. By way of example, treating a heart condition may include, in whole or in part, i) identifying a progression of heart failure over time; ii) confirming an arrhythmia identified by an arrhythmia detection process; iii) instructing the patient to perform a posture recalibration procedure and/or iv) delivering a therapy.

The terms "beat" and "cardiac event" are used interchangeably and refer to both normal and/or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, an unhealthy or abnormal functioning of the heart.

The term "real-time" refers to a time frame contemporaneous with normal or abnormal episode occurrences. For example, a real-time process or operation would occur during or immediately after (e.g., within minutes or seconds after) a cardiac event, a series of cardiac events, an arrhythmia episode, and the like.

The term "adaptive", as used in connection with a sensitivity profile, sensitivity limit, sensitivity level or other sensing parameters, refers to an ability of the processes herein to modify the value of sensitivity and/or sensing parameters based on Cal within the CA signals exceeding a COI threshold and determining that one or more of a patient posture or a respiration cycle at least in part caused the COI to exceed the COI threshold. The sensitivity profile parameters may include refractory period, start sensitivity, decay delay, sensitivity limit, slope of sensitivity decay, etc.

The term "sensitivity level", as used herein, refers to a threshold that an input CA signal must exceed for an implantable device to identify a CA signal feature of interest (e.g., an R-wave). As one non-limiting example, software may be implemented using a programmed sensitivity level to declare an R-wave to be detected when the input CA signal exceeds the current programmed sensitivity level. In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with amplitude of 0.14 mV will not be detected as an R-wave. Embodiments herein determine an adaptive sensitivity limit and sensitivity profile for the sensitivity level.

The term "device documented feature marker" refers to markers that are declared by an implantable cardiac monitor and/or implantable medical device. Any or all of the foregoing examples of markers represent device document markers. Markers may be declared based on numerous criteria, such as signal processing, feature detection and arrhythmia detection software and hardware within and/or operating on the implantable cardiac monitor and/or implantable medical device.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection.

The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

System for Labeling Arrhythmias

In accordance with embodiments herein, methods and systems are provided for reducing false declarations of cardiac events due to undersensing or oversensing of R-waves of the CA signals for a series of beats. Such methods and systems detect motion data indicative of at least one of a respiration cycle and/or patient posture and adaptively manage a sensitivity of a sensitivity profile based thereon. Adaptively managing the sensitivity of the sensitivity profile at least reduces false declarations of cardiac events due to undersensing or oversensing of R-waves of the CA signals. Embodiments herein increase the quality of life and improve the long-term management of relevant patient populations by managing (e.g., reducing or eliminating) false declarations of cardiac events, false declarations of physiological status, and/or unnecessary administration of therapies and/or interventions.

In accordance with embodiments herein, the IMD includes an accelerometer to collect accelerometer signatures indicative of motion data of the corresponding cardiac beats. Motion data is indicative of at least one of a patient posture or a respiration cycle. The accelerometer may provide data and/or accelerometer signatures indicative of motion data. The accelerometer signatures indicative of motion data may be used to identify whether the COI of the CA signals for the series of beats from at least a first segment of the CA signals exceeds a COI limit. In one example, the COI limit may represent at least one of an expected variability of an R-wave or a presence of the R-wave. The acceleration signatures indicative of motion data may also be used to determine whether at least one of the patient posture or the respiration cycle at least in part caused the COI to exceed the COI limit. In one example, baseline motion data is indicative of at least one of a supine baseline posture or a baseline respiration cycle. Motion data is compared to the baseline motion data to identify motion changes that are associated with changes in an amplitude of the CA signals that occur with different postures and minute ventilation increase and decrease changes.

In accordance with additional or alternative embodiments herein, the IMD includes an impedance monitor to collect impedance signatures indicative of motion data of a respiration cycle of the corresponding cardiac beats. The impedance monitor may provide data and/or impedance signatures indicative of motion data of the respiration cycle. The impedance signatures indicative of motion data may be used to identify whether the COI of the CA signals for the series of beats from at least a first segment of the CA signals exceeds a COI limit. In one example, the COI limit may represent at least one of an expected variability of an R-wave or a presence of the R-wave. The impedance signatures indicative of motion data of the respiration cycle may also be used to determine whether the respiration cycle at least in part caused the COI to exceed the COI limit. In one example, baseline motion data is indicative of a baseline respiration cycle. Motion data is compared to the baseline motion data to identify motion changes that are associated with changes in an amplitude of the CA signals that occur with minute ventilation increase and decrease changes.

In one example, methods and systems are provided in accordance with embodiments herein that decrease a sensitivity (or increase the resolution) of a sensing profile of a sensing circuit of the IMD based on determining that the posture and/or respiration cycle reduced the amplitude of the CA signals by an amount sufficient to cause the COI to exceed the COI limit. The sensing circuit continues to decrease the sensitivity until either a sensitivity limit is reached, or an amplitude of the CA signals exceeds the sensing profile, such that a new sensed R-wave is detected. Accordingly, using one or more of accelerometer signatures indicative of motion data and impedance signatures indicative of minute ventilation in conjunction with CA signals affords a powerful, sophisticated process to for reducing false declarations of arrhythmias.

Embodiments may be implemented in connection with one or more implantable medical devices (IMDs). Non-limiting examples of IMDs include one or more of neurostimulator devices, implantable cardiac monitoring and/or therapy devices. For example, the IMD may represent a cardiac monitoring device, pacemaker, cardioverter, cardiac rhythm management device, defibrillator, neurostimulator, leadless monitoring device, leadless pacemaker, an external shocking device (e.g., an external wearable defibrillator), and the like. For example, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Additionally or alternatively, the IMD may include one or more structural and/or functional aspects of the device(s) described in U.S. Pat. No. 9,333,351 "Neurostimulation Method and System to Treat Apnea" and U.S. Pat. No. 9,044,710 "System and Methods for Providing A Distributed Virtual Stimulation Cathode for Use with an Implantable Neurostimulation System", which are hereby incorporated by reference. Further, one or more combinations of IMDs may be utilized from the above incorporated patents and applications in accordance with embodiments herein.

Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device and Method Including the Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device", U.S. Pat. No. 9,232,485 "System and Method for Selectively Communicating with an Implantable Medical Device", EP Application No. 0070404 "Defibrillator" and, U.S. Pat. No. 5,334, 045 "Universal Cable Connector for Temporarily Connecting Implantable Leads and Implantable Medical Devices with a Non-Implantable System Analyzer", U.S. patent application Ser. No. 15/973,126, titled "Method And System For Second Pass Confirmation Of Detected Cardiac Arrhythmic Patterns"; U.S. patent application Ser. No. 15/973,351, Titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns" which are hereby incorporated by reference.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method and System to Discriminate Rhythm Patterns in Cardiac Activity"; U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns", which are expressly incorporated herein by reference.

FIG. 1 illustrates an implantable medical device (IMD) 100 intended for subcutaneous implantation at a site near the heart. The IMD 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the IMD 100, while the electrode 126 is located on a proximal side of the IMD 100. Additionally or alternatively, electrodes 126 may be located on opposite sides of the IMD 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.).

The housing 102 includes various other components such as: sense electronics for receiving signals from the electrodes, a microprocessor for analyzing the far field CA signals, including assessing the presence of R-waves in cardiac beats occurring while the IMD is in different IMD locations relative to gravitational force, a loop memory for temporary storage of CA data, a device memory for long-term storage of CA data, sensors for detecting patient activity, including an accelerometer for detecting acceleration signatures indicative of heart sound, and a battery for powering components.

In at least some embodiments, the IMD 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The IMD 100 may be configured to be activated by the patient or automatically activated, in connection with recording subcutaneous ECG signals.

The IMD 100 senses far field, subcutaneous CA signals, processes the CA signals to detect arrhythmias and if an arrhythmia is detected, automatically records the CA signals in memory for subsequent transmission to an external device 154.

The IMD 100 is implanted in a position and orientation such that, when the patient stands, the IMD 100 is located at a reference position and orientation with respect to a global coordinate system 10 that is defined relative to a gravitational direction 12. For example, the gravitational direction 12 is along the Z-axis while the X-axis is between the left and right arms.

As explained herein, the IMD 100 includes electrodes that collect cardiac activity (CA) signals in connection with multiple cardiac beats and in connection with different IMD locations (e.g., different positions and/or different orientations). The IMD may change location within a subcutaneous pocket relative to an initial implant position through translation and/or rotation, such as i) moving up and down (elevating/heaving) within the subcutaneous pocket; ii) moving left and right (strafing/swaying); iii) moving forward and backward (walking/surging); iv) swiveling left and right (yawing); v) tilting forward and backward (pitching); and pivoting side to side (rolling). The IMD 100 also includes one or more sensors to collect device location information indicative of movement of the IMD 100 along one or more degrees of freedom, namely translational motion along X, Y, and Z directions, and/or rotationally motion along pitch, yaw and/or roll directions.

The IMD 100 also includes one or more sensors to collect acceleration signatures that are indicative of heart sounds produced at different points in a cardiac cycle.

Figure 2A:
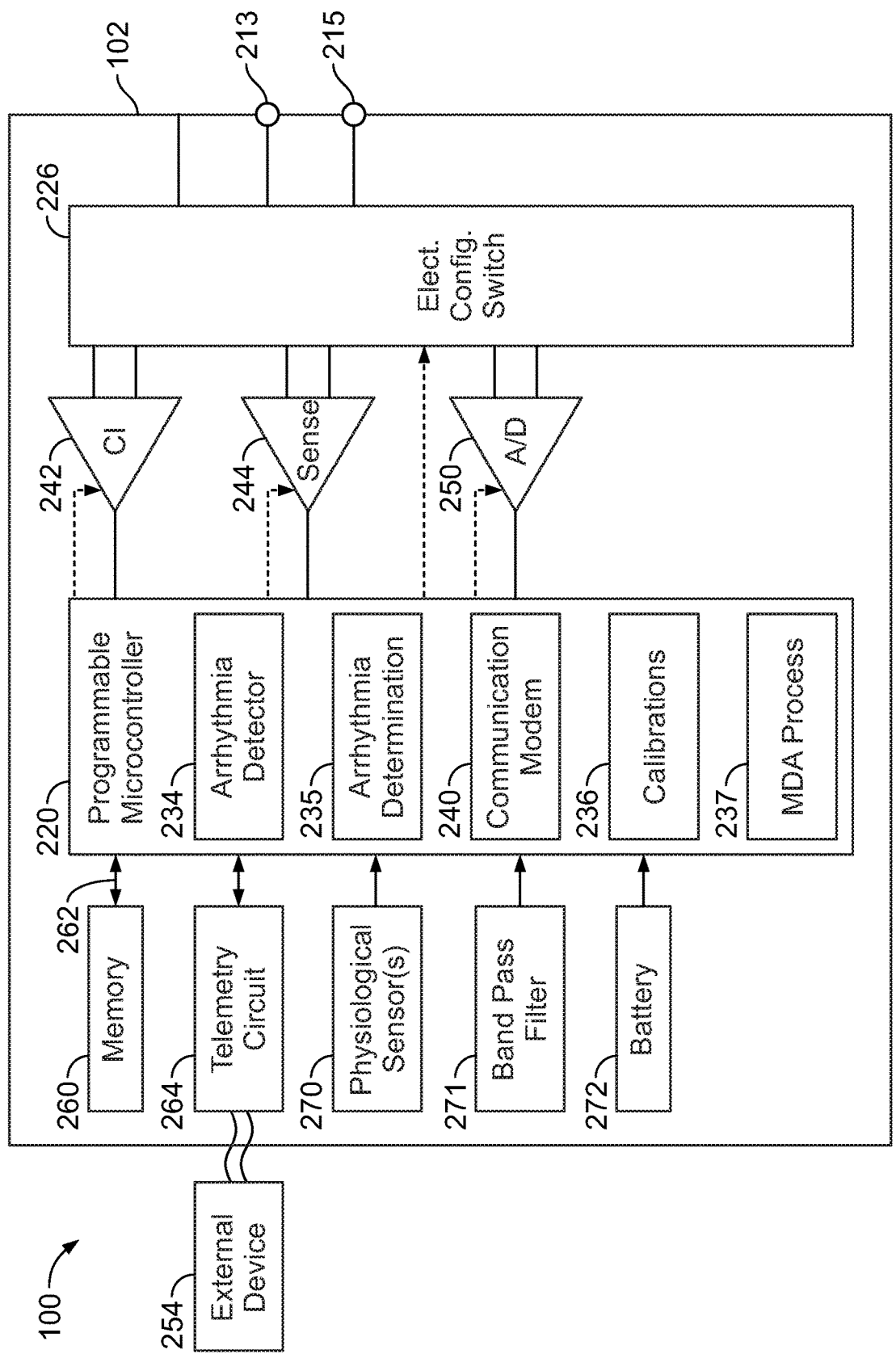
FIG. 2A illustrates a block diagram of an IMD formed in accordance with embodiments herein.

FIG. 2A shows an example block diagram of the IMD 100 formed in accordance with embodiments herein. The IMD 100 may be implemented to monitor ventricular activity alone, or both ventricular and atrial activity through sensing circuit. The IMD 100 has a housing 102 to hold the electronic/computing components. The housing 102 (which is often referred to as the "can," "case," "encasing," or "case electrode") may be programmably selected to act as an electrode for certain sensing modes. Housing 102 further includes a connector (not shown) with at least one terminal 213 and optionally additional terminals 215. The terminals 213, 215 may be coupled to sensing electrodes that are provided upon or immediately adjacent the housing 102. Optionally, more than two terminals 213, 215 may be provided in order to support more than two sensing electrodes, such as for a bipolar sensing scheme that uses the housing 102 as a reference electrode. Additionally or alternatively, the terminals 213, 215 may be connected to one or more leads having one or more electrodes provided thereon, where the electrodes are located in various locations about the heart. The type and location of each electrode may vary.

The IMD 100 includes a programmable microcontroller 220 that controls various operations of the IMD 100, including cardiac monitoring. Microcontroller 220 includes a microprocessor (or equivalent control circuitry), RAM and/or ROM memory, logic and timing circuitry, state machine circuitry, and I/O circuitry. Microcontroller 220 includes an arrhythmia detector 234 that is configured to analyze the far field cardiac activity signals to identify the existence of an arrhythmia. The microcontroller 220 also includes arrhythmia determination circuitry 235 for analyzing the CA signals to assess a presence or absence of R-waves within the cardiac beats from a first segment of the CA signals, and detect an arrhythmia based on the presence or absence of one or more R-waves from the cardiac beats within a second segment of the CA signals.

The microcontroller 220 also includes a motion data analysis (MDA) process 237 configured to identify whether a COI from a first segment of the CA signals exceeds a COI limit, analyze motion data to determine whether the at least one of the posture or the respiration cycle at least in part caused the COI to exceed the COI limit, and, based on the analyze, and adjust a CA sensing parameter utilized by the IMD 100 to detect R-waves in subsequent CA signals as described in greater detail below. Consequently, arrhythmia detection accuracy is increased and false declarations of arrhythmias are reduced.

The MDA process 237 is configured to implement one or more of the operations discussed herein. The MDA process 237 is configured to be a computer implemented method for reducing false declarations of arrhythmias based on oversensing or undersensing of R-waves of the CA signals. The MDA process 237 obtains CA signals, at the electrodes of the IMD 100, in connection with multiple cardiac beats and, in connection with the CA signals, obtains motion data indicative of one or more of a patient posture or a respiration cycle. The method obtains motion data at one or more physiological sensors 270 (e.g., an accelerometer) and/or via a cardiac impedance (CI) sensing circuit 242 of the IMD 100 generated during the cardiac beats. The MDA process 237 identifies whether a COI from a first segment of the CA signals exceeds a COI limit and analyzes motion data to determine whether the at least one of the posture or the respiration cycle at least in part caused the COI to exceed the COI limit. Based on the analyzing operation, the MDA process 237 automatically adjusts the CA sensing parameter utilized by the IMD 100 to detect R-waves in subsequent CA signals. The CA sensing parameter defines a sensitivity profile. The MDA process 237 automatically adjusts the CA sensing parameter by changing a sensitivity of the sensitivity profile to at least reduce false arrhythmia detection due to undersensing or oversensing of R-waves. Based on the adjusted CA sensing parameter, the arrhythmia determination circuitry 235 detects an arrhythmia based on the presence or absence of one or more of the R-waves in at least the second segment of the CA signals.

Figure 2B:
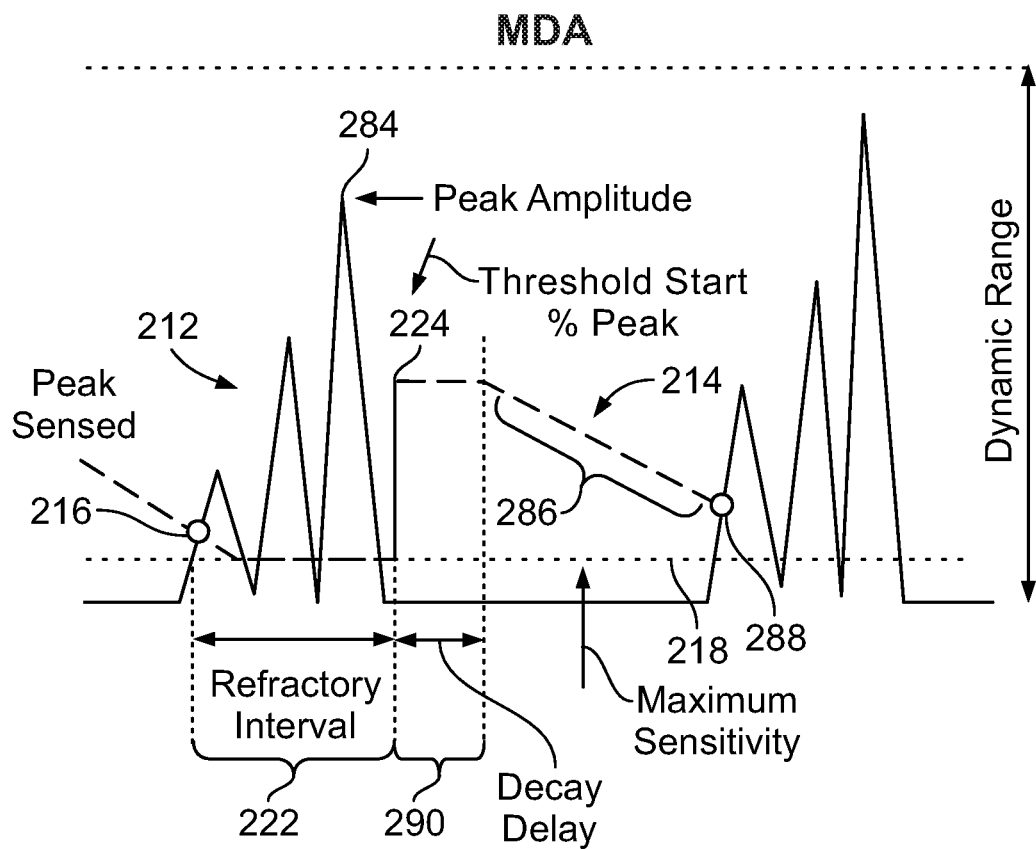
FIG. 2B illustrates an automatic sensing adjustment utilized by the motion data analysis (MDA) process of the IMD in accordance with embodiments herein.

FIG. 2B illustrates an automatic sensing adjustment utilized by the MDA process 237 of the IMD 100 in accordance with embodiments herein. FIG. 2B illustrates an example CA signal 212 after passing through a rectifier to convert all positive and negative deflections within the CA signal 212 to be positive deflections. The MDA process 237 manages the sensing circuit 244 to have a sensitivity profile 214 (denoted by a dashed line) that varies over time.

In a basic implementation, the MDA process 237 utilizes an automatic sensing adjustment based on the sensitivity profile 214. The sensitivity profile 214 is defined by sensitivity profile parameter settings corresponding to the threshold start sensitivity 224, decay delay parameter 290, sensitivity limit 218 and slope of the sensitivity decay 286. Optionally, the sensitivity decay 286 may be defined in accordance with a non-linear monotonically changing shape from the threshold start sensitivity 224 to the sensitivity limit 218. The start sensitivity parameter defines a start sensitivity of the sensitivity profile. For example, the start sensitivity parameter may set start sensitivity to a percentage of the preceding R-wave peak amplitude. The refractory period/interval duration parameter defines a blanking interval beginning at a sensed R-wave, during which the processors do not search for a T-wave. The decay delay parameter defines the interval at which the sensitivity profile maintains the sensitivity level at a constant level following expiration of the refractory period before the sensitivity profile begins decreasing. When the sensitivity profile includes a linear sensitivity level decline, the decay delay rate defines a slope of the linear sensitivity level decline. The sensitivity limit defines a lowest sensitivity level (e.g., maximum resolution) that linear sensitivity decline is allowed to reach. The sensitivity parameters are initially programmed to values based on baseline motion data and, over the operation of the IMD 100, are automatically adjusted based on determining that at least one of the patient posture or the respiration cycle at least in part caused the COI of the CA signals to exceed the COI limit.

In accordance with the sensitivity profile 214, when the CA signal 212 crosses the sensitivity profile 214 at starting point 216, the MDA process 237 treats the point 216 as a sensed R-wave and begins a refractory interval 222. No new R-wave (or T-wave) will be sensed during the refractory interval 222. At the end of the refractory interval 222, the sensitivity is adjusted to a threshold start sensitivity 224. The threshold start sensitivity 224 is defined as a percentage of the peak amplitude 284 of the QRS complex of the CA signal 212 detected during the refractory interval 222. The sensing circuit 244 maintains the threshold start sensitivity 224 for a decay delay parameter 290, after which the MDA process 237 begins to monotonically decrease the sensitivity (increase the resolution) of the sensing circuit 244 as denoted by the sensitivity decay 286 within the sensitivity profile 214. The sensing circuit 244 continues to decrease the sensitivity until either the sensitivity decay 286 reaches the sensitivity limit 218 or an amplitude of the rectified CA signal 212 exceeds the sensor sensitivity profile 214, such as at a point 288 where a new sensed R wave is detected.

The sensitivity of the sensing circuit 244 is continuously adjusted by the microcontroller 220 in accordance with the sensitivity profile 214 over the course of an individual cardiac event. Furthermore, the MDA process 237 modifies a sensitivity of the sensitivity profile of the CA sensing parameter to at least reduce false arrhythmia detection due to undersensing or oversensing R-waves on at least one of i) beat by beat, or ii) for ensembles of beats. For detection for ensembles of beats, a monitoring window (e.g., 10s-30s) may be implemented to ensure the posture is stable over a given ensemble of beats (e.g., a moving average over the monitoring window). For example, a patient may change posture from a standing posture to a supine posture in 1 second, but changes in R-waves resulting from the change in posture from the standing posture to the supine posture may take additional time (e.g., 3-4 seconds). In additional or alternative embodiments, the MDA process 237 may monitor undersensing or oversensing of R-waves on both i) beat by beat, and ii) for ensembles of beats, and based on the posture being stable over the monitoring window, modify the sensitivity of the sensitivity profile due to undersensing or oversensing R-waves based on the ensembles of beats. Conversely, the MDA process 237 may monitor undersensing or oversensing of R-waves on both i) beat by beat, and ii) for ensembles of beats, and based on the posture being unstable (or not being stable) over the monitoring window, modify the sensitivity of the sensitivity profile due to undersensing or oversensing R-waves on a beat by beat basis. The MDA process 237 may determine, on a beat by beat basis, whether to monitor R-waves on based on i) beat by beat, or ii) for ensembles of beats.

In accordance with embodiments herein, a sensitivity of the sensitivity profile parameters may be adjusted based on the MDA process 237 determining whether at least one of the posture or the respiration cycle at least in part caused the COI to exceed the COI limit. False arrhythmia detection may occur in connection with the COI exceeding the COI limit which may arise from undersensing of R-waves and/or oversensing of R-waves (e.g., sensing noise, or P-waves, or T-waves as R-waves). For example, based on the MDA process 237 determining that at least one of the patient posture or the respiration cycle at least in part caused the COI to exceed the COI limit, the MDA process 237 automatically adjusts the sensitivity of the sensitivity profile parameters. The MDA process 237 may continue to decrease the sensitivity until either a sensitivity limit is reached, or an amplitude of the CA signals exceeds the sensing profile, such that a new sensed R-wave is detected. Additionally or alternatively, portions of the MDA process may be implemented external to the IMD 100, such as at a local external device or remote server. The local external device and/or remote server may return, to the IMD 100, adjustments to the sensitivity profile parameters based on an externally implemented portions of the MDA process 237 determining whether at least one of the posture or the respiration cycle at least in part caused the COI to exceed the COI limit.

The microcontroller 220 may also include calibration circuitry 236 that obtains calibration acceleration signatures at an accelerometer, or physiological sensor 270 that is indicative of motion data in connection with at least one of a patient posture or a respiration cycle of a patient. For example, the postures may include supine, laying on a right side, laying on a left side, or the like. In one example, the acceleration signatures are indicative of motion data generated in connection with first and second postures of a patient. After the calibration procedure, the calibration circuitry 236 utilizes the calibration acceleration signatures to determine an axis of the accelerometer associated with a current posture. The confirmation acceleration signatures are obtained along the axis of the accelerometer in connection with obtaining motion data indicative of a posture.

Although not shown, the microcontroller 220 may further include other dedicated circuitry and/or firmware/software components that assist in monitoring various conditions of the patient's heart and managing pacing therapies.

A switch 226 is optionally provided to allow selection of different electrode configurations under the control of the microcontroller 220. The electrode configuration switch 226 may include multiple switches for connecting the desired electrodes to the appropriate I/O circuits, thereby facilitating electrode programmability. The switch 226 is controlled by a control signal from the microcontroller 220. Optionally, the switch 226 may be omitted and the I/O circuits directly connected to a housing electrode.

The IMD 100 is further equipped with a communication modem (modulator/demodulator) 240 to enable wireless communication. In one implementation, the communication modem 240 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 240 may be implemented in hardware as part of the microcontroller 220, or as software/firmware instructions programmed into and executed by the microcontroller 220. Alternatively, the modem 240 may reside separately from the microcontroller as a standalone component. The modem 240 facilitates data retrieval from a remote monitoring network. The modem 240 enables timely and accurate data transfer directly from the patient to an electronic device utilized by a physician.

The IMD 100 includes the CI sensing circuit 242 selectively coupled to one or more electrodes that perform sensing operations through the switch 226 to detect impedance data. For example, the CI sensing circuit 242 is coupled to various combinations of electrodes. The CI sensing circuit 242 collects impedance data by measuring voltage potentials and generating an impedance related voltage measurement stream (also referred to as an impedance data stream) associated with a corresponding CI sensing vector. The CI sensing circuit 242 is coupled to the switch 226 which connects the CI sensing circuit 242 so that voltage signals, related to impedance, at any desired electrode may be obtained. The CI sensing circuit 242, the switch 226 and the electrodes connected thereto define one or more CI sensing channels. The CI sensing channels are utilized to obtain at least one of thoracic impedance measurements or cardiogenic impedance measurements, as impedance signatures, for respiration cycles. The impedance signature for a respiration cycle is indicative of values of the components of minute ventilation in accordance with embodiments herein.

Figure 4A:
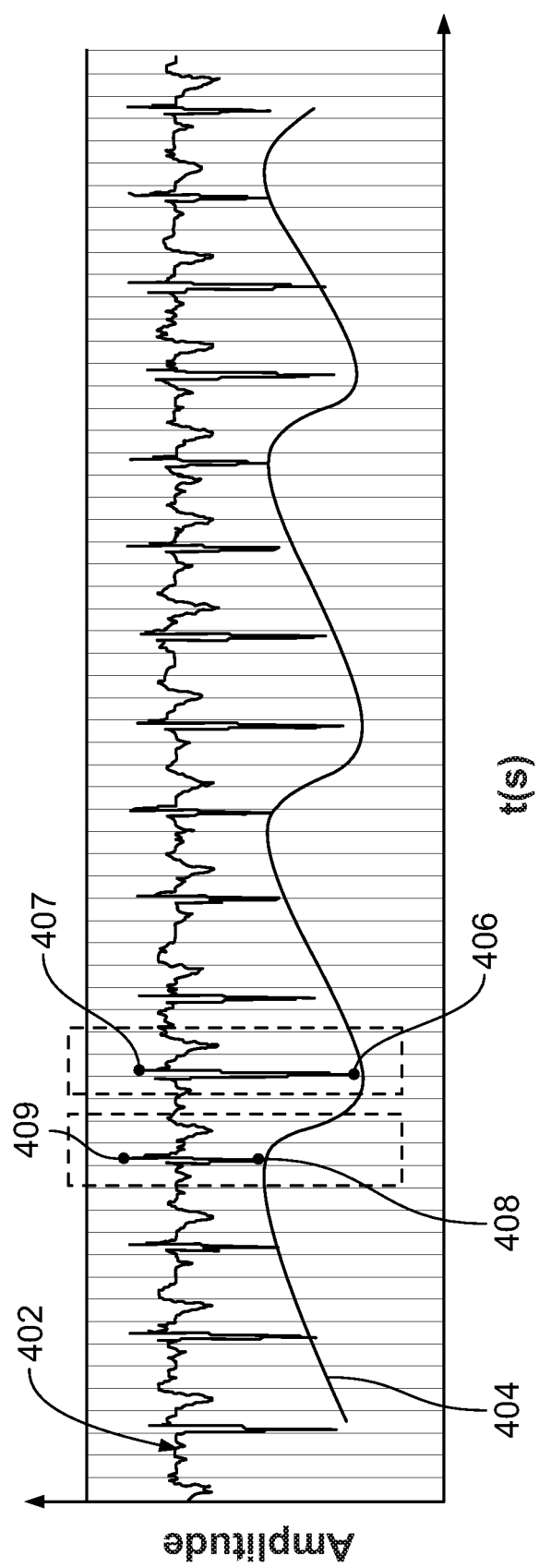
FIG. 4A illustrates one example of R-wave amplitude change with a respiration cycle in accordance with embodiments herein.

FIG. 4A illustrates one example of R-wave amplitude change with a respiration cycle in accordance with embodiments herein. For a CA signal 402 measured over time (e.g., seconds), R-wave amplitude varies over the course of a respiration cycle 404. For example, with a normal breathing rate and heart rate relationship (e.g., at rest, corresponding to 75 beats per minute and 10-12 breaths per minute), the R-wave amplitude 407 is significantly reduced during peak expiration 406 compared to the R-wave amplitude 409 during peak inspiration 408.

Figure 4B:
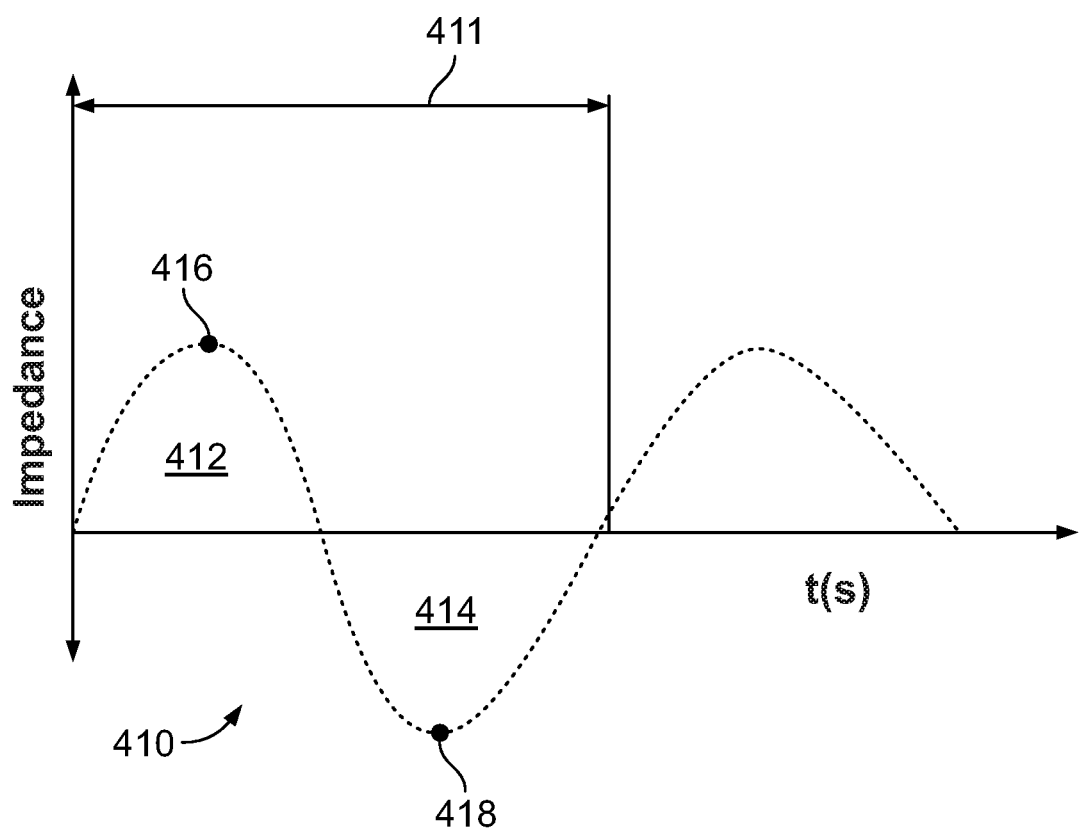
FIG. 4B illustrates one example of a zero-crossing wave form generated by measuring impedance during a respiration cycle in accordance with embodiments herein.

FIG. 4B illustrates one example of a zero-crossing wave form generated by measuring impedance during a respiration cycle in accordance with embodiments herein. In accordance with embodiments herein, the impedance signature indicative of the respiratory components of minute ventilation (e.g., respiratory rate and tidal volume) may be measured via the impedance differences generated by, e.g., causing the CI sensing circuit 242 to send a constant impedance signal from a first electrode of the housing 102 to a second electrode (e.g., an electrode of an intracardiac or epicardial pacing lead or the like) and monitoring the return voltage back to the housing 102. From the impedance signature, a zero-crossing wave form may be generated that provides a respiratory cycle 410 that may be measured with respect to areas above 412 (e.g., corresponding to an inhale) and below 414 (e.g., corresponding to an exhale) for one cycle (e.g., breath 411) of the respiratory cycle 410. Furthermore, the peak inspiration 416 and peak expiration 418 of the respiration cycle may be identified and correlated to the CA signals of the series of cardiac beats.

The IMD 100 includes sensing circuit 244 selectively coupled to one or more electrodes that perform sensing operations through the switch 226 to detect CA data indicative of cardiac activity. The sensing circuit 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 226 may be used to determine the sensing polarity of the CA signal by selectively closing the appropriate switches.

In the example of FIG. 2A, a single sensing circuit 244 is illustrated. Optionally, the IMD 100 may include multiple sensing circuits, similar to sensing circuit 244, where each sensing circuit is coupled to two or more electrodes and controlled by the microcontroller 220 to sense electrical activity detected at the corresponding two or more electrodes. The sensing circuit 244 may operate in a unipolar sensing configuration or a bipolar sensing configuration. Optionally, the sensing circuit 244 may be removed entirely, and the microcontroller 220 perform the operations described herein based upon the CA signals from the ND data acquisition system 250 directly coupled to the electrodes. The output of the sensing circuit 244 is connected to the microcontroller 220 which, in turn, determines when to store the CA data of the CA signals (digitized by the ND data acquisition system 250) in the memory 260. The CA signals and motion data are analyzed to determine if the COI had exceeded the COI limit and if the at least one of the posture or the respiration cycle at least part caused the COI to exceed the COI limit.

The IMD 100 further includes an analog-to-digital A/D data acquisition system (DAS) 250 coupled to one or more electrodes via the switch 226 to sample CA signals across any pair of desired electrodes. The MDA process 237 may be applied to signals from the sensing circuit 244 and/or the DAS 250.

By way of example, the external device 254 may represent a bedside monitor installed in a patient's home and utilized to communicate with the IMD 100 while the patient is at home, in bed or asleep. The external device 254 may be a programmer used in the clinic to interrogate the IMD 100, retrieve data and program detection criteria and other features. The external device 254 may be a handheld device (e.g., smartphone, tablet device, laptop computer, smartwatch and the like) that may be coupled over a network (e.g., the Internet) to a remote monitoring service, medical network and the like. The external device 254 may communicate with a telemetry circuit 264 of the IMD through a communication link 266. The external device 254 facilitates access by physicians to patient data as well as permitting the physician to review real-time CA signals while collected by the IMD 100.

The microcontroller 220 is coupled to a memory 260 by a suitable data/address bus 262. The memory 260 stores the motion data, baseline motion data sets, CA signals, as well as the markers and other data content associated with detection and determination of the arrhythmia.

The IMD 100 may further include one or more physiologic sensors 270. For example, the physiologic sensor 270 may represent one or more accelerometers, such as a three-dimensional (3D) accelerometer. The sensor 270 may utilize a piezoelectric, a piezoresistive, and/or capacitive components are commonly used to convert the mechanical motion of the 3D accelerometer into an electrical signal received by the microcontroller 220. By way of example, the 3-D accelerometer may generate three electrical signals indicative of motion in three corresponding directions, namely X, Y and Z directions. The electrical signals associated with each of the three directional components may be divided into different frequency components to obtain different types of information therefrom.

The physiologic sensor 270 collects device location information with respect to gravitational force while the IMD 100 collects CA signals in connection with multiple cardiac beats. The microcontroller 220 may utilize the signals from the physiologic sensor 270 in the manner described in U.S. Pat. No. 6,937,900, titled "AC/DC Multi-Axis Accelerometer for Determining A Patient Activity and Body Position," the complete subject matter which is expressly incorporated herein by reference. While shown as being included within the housing 102, the physiologic sensor(s) 270 may be external to the housing 102, yet still, be implanted within or carried by the patient.

The physiologic sensor 270 may be further configured to obtain motion data in the form of acceleration signatures generated during cardiac beats. The acceleration signatures from the sensor 270 are provided to the microcontroller 220 and are analyzed by the MDA process 237. The motion data is indicative of one or more of the patient posture or the respiration cycle.

Figure 5A:
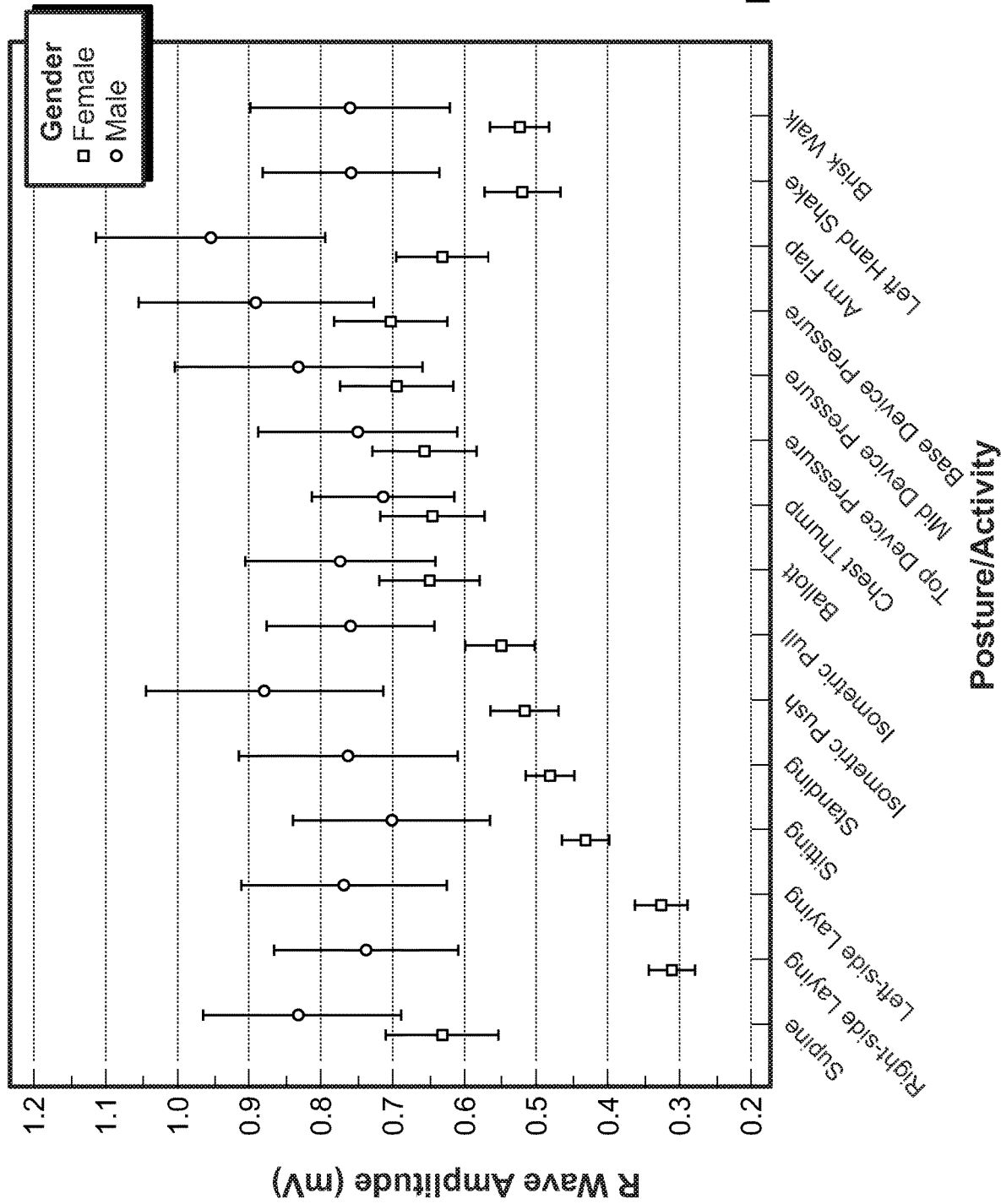
FIG. 5A is a graph illustrating examples of the impact on R-wave amplitude due to patient posture and physical activity.

FIG. 5A is a graph illustrating examples of the impact on R-wave amplitude due to patient posture and physical activity in accordance with embodiments herein. The sensor 270 varies readings as a result of the posture or changes in posture of the patient. For example, patients may change posture while monitoring occurs during sleep, i.e., sleeping on a left side, sleeping on a right side, supine, prone, 45 degree inclined, etc., which may impact the CA signals for the series of beats, leading to potential variation in CA signals that may result in the IMD 100 oversensing or undersensing R-waves. For example, the R-wave amplitudes measured for supine posture 502 are highest and R-wave amplitudes measured for right side laying posture 504 are lowest for female patients compared across a series of patient postures and/or activities. The R-wave amplitudes of patient postures and/or activities increases from right side laying through the progression to left side laying, sitting, standing, isometric pushing, isometric pulling, and the like. The variation in CA signals across postures may also be different between male patients and female patients, and the degree of amplitude variation may be patient unique. If the IMD 100 is placed on a flat surface, the z-axis of the accelerometer indicates 1 g (gravity) while the x and y axis gravity data are zero because each axis is perpendicular to gravity. If the patient changes posture, a new position is represented by a unique combination of x, y, z values with respect to gravity. As such, the position of the IMD is indicative of gravity influencing 3-axis of the accelerometer that is unique to a particular posture and may be correlated to an impact of the posture or change in posture on R-wave sensing.

In accordance with embodiments herein, the IMD 100 may determine and store the R-wave amplitude during supine posture as baseline motion data. The baseline motion data is indicative of at least one of a supine baseline posture or a baseline respiration cycle. A database or algorithm stored in the memory of the IMD 100 may provide further baseline motion data values related to the expected variability in CA signals between postures and points in the respiration cycle.

Figure 5B:
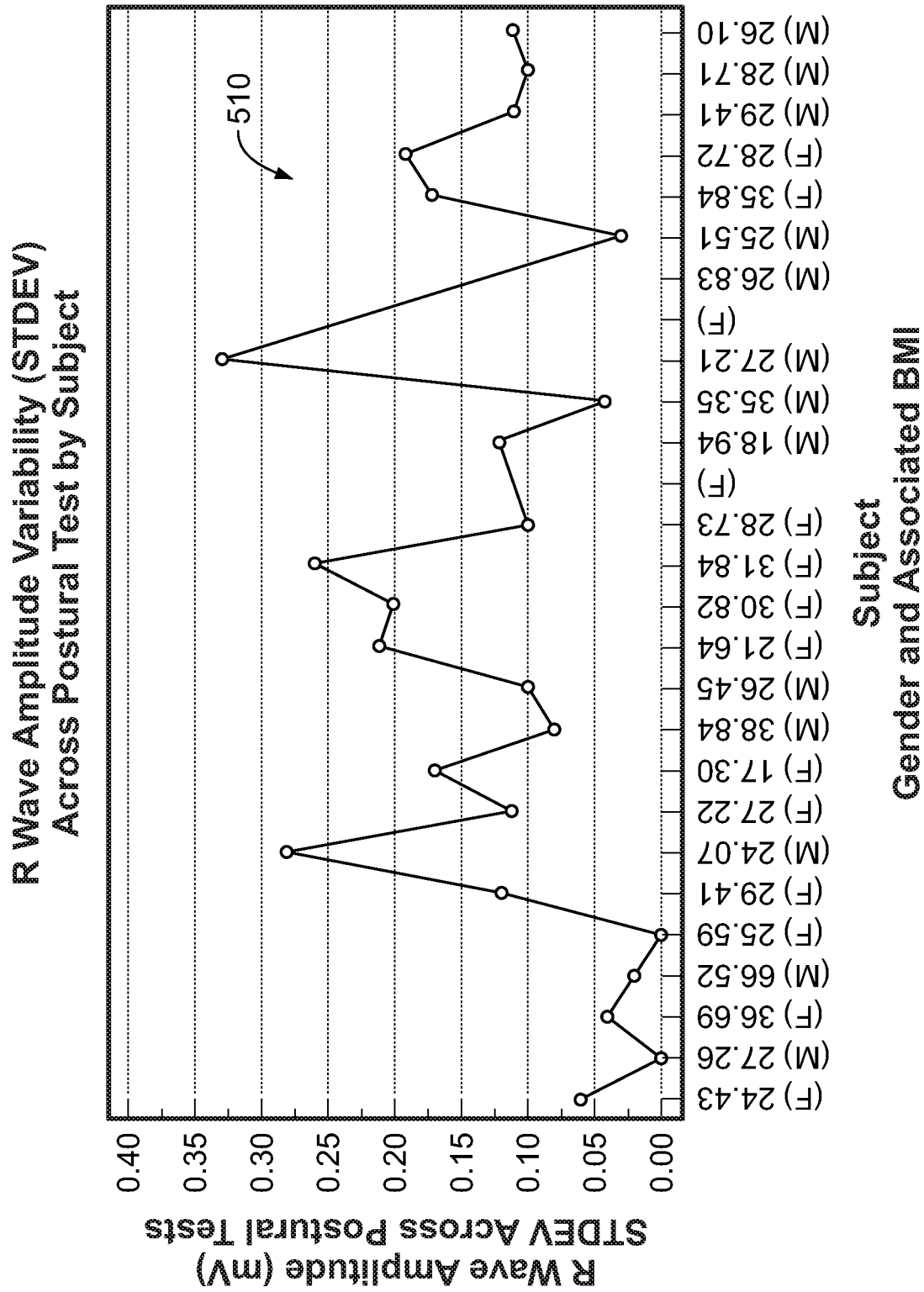
FIG. 5B illustrates one example of a database or algorithm 510 of R-wave amplitudes in accordance with embodiments herein.

FIG. 5B illustrates one example of a database or algorithm 510 of R-wave amplitudes in accordance with embodiments herein. The database or algorithm 510 may include expected standard deviations of R-wave amplitudes (as measured along the y-axis) for different genders and body mass index values across a number of different postures (as identified along the x-axis). In the example, expected R-wave amplitudes are determined based on supine, right-side laying, left-side laying, sitting, standing, isometric arm activities, device manipulation, arm exercise, and brisk walking for patients having different genders and BMIs (e.g., at 0 for male patients having a BMI of 27.26, at 0.26 for female patients having a BMI of 31.24, etc.). Based on subsequent changes in CA signals, the CA signals may be compared with the corresponding motion data and the baseline motion data to evaluate if the changes in CA signals (e.g., R-waves, R-wave amplitudes) resulted at least in part to changes in at least one of the posture or the respiration cycle.

In an additional or alternative example, the sensor 270 varies readings as a result of changes that occur during a respiration cycle, such as the respiration cycles of FIG. 4A-4B. The variability of R-wave amplitude, as the COI limit, may be determined across a plurality (e.g., 6) cardiac cycles and a corresponding plurality of resting respiratory cycles (e.g., 10) for each posture of a series of postures. R-wave amplitude varies over a respiration cycle for a single posture. Furthermore, patients may change posture while monitoring occurs during sleep, i.e., sleeping on a left side, sleeping on a right side, supine, prone, 45 degree inclined, etc., which may impact the CA signals for the series of beats, leading to potential variation in CA signals that may result in the IMD 100 oversensing or undersensing R-waves.

Figure 5C:
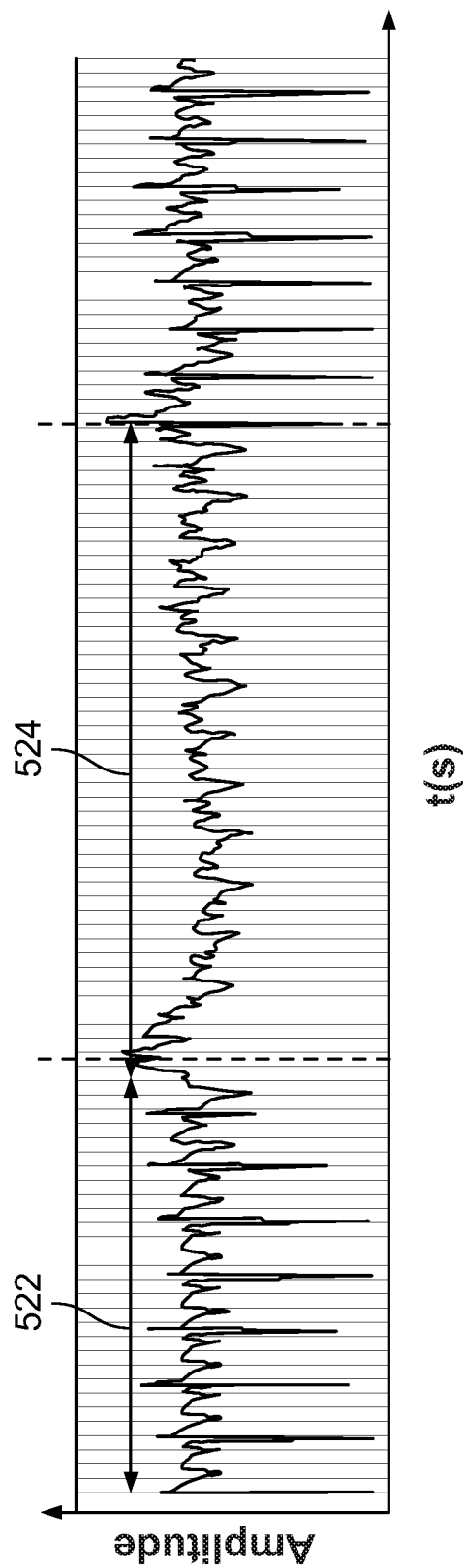
FIG. 5C illustrates one example of R-wave variation in response to a respiration cycle and a postural change in accordance with embodiments herein.

FIG. 5C illustrates one example of R-wave variation in response to a respiration cycle and a postural change in accordance with embodiments herein. For example, the R-wave amplitudes measured for respiration cycles during a supine posture 522 are higher than R-wave amplitudes measured respiration cycles during right side laying posture 524. In one example, based on the one or more processors sensing that the R-wave amplitude of the CA signals occurs below an expected variability of an amplitude of an R-wave for a select posture, the MDA process 237 lowers the sensitivity of the sensing profile, thereby setting a new value for the expected variability of an amplitude of an R-wave associated with the select posture. In an additional or alternative example, based on the one or more processors sensing both variation of R-wave amplitude within the expected variability of the R-wave and an abrupt change in R-wave amplitude outside of the expected variability of the R-wave due to a change in posture, the change in posture invokes a temporary lowering of the expected variability of the R-wave.

Figure 5D:
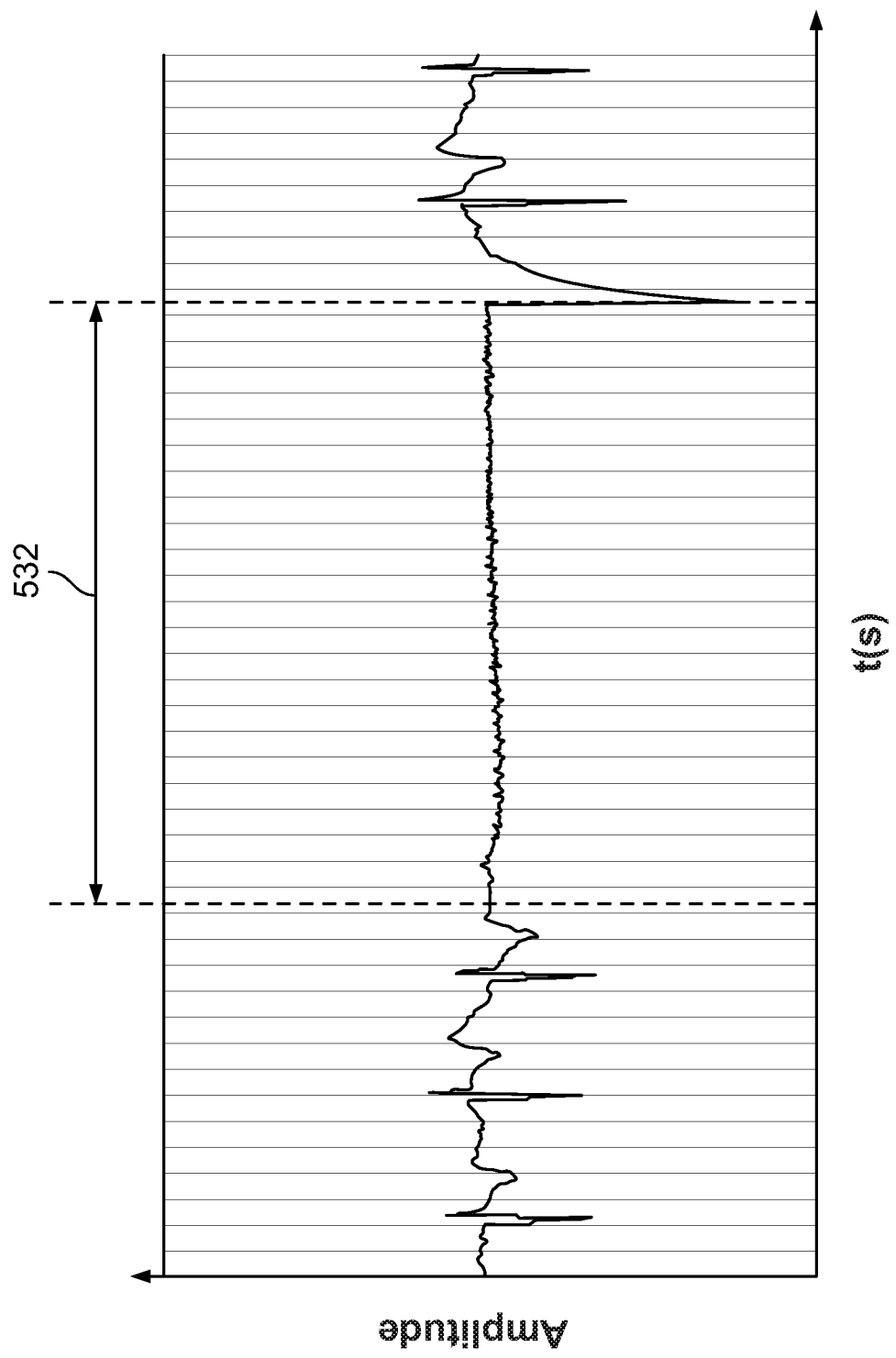
FIG. 5D illustrates one example of R-wave variation in response to noise and/or loss of contact (LOC) events in accordance with embodiments herein.

FIG. 5D illustrates one example of R-wave variation in response to noise and/or loss of contact (LOC) events in accordance with embodiments herein. Noise and/or loss of contact (LOC) events may be distinguished from physiological CA signals based on, e.g., one or more of amplitude or frequency characteristics falling outside of a physiological range. In the presence of noise and/or LOC event 532, there will be a complete loss of the R-wave accompanied by a substantial rise in the frequency of amplitude events and lowering of the amplitude. This pattern typically occurs outside of the rates associated with physiological CA signals and may be distinguished and declared by the MDA process 237 based thereon. The MDA process 237 may temporarily suspend detection of the CA signals the amplitude of the R-waves of the CA signals reaches the bottom threshold of the expected variability of the R-wave. For example, based on a noise and/or an LOC event being detected (e.g., the expected variability of the R-wave exceeds two standard deviations), the MDA process 237 may stop decrementing the sensitivity of the sensitivity profile and maintain the current sensitivity until a change in posture is detected. Once a change in posture is detected, the MDA process 237 may resume detection of the CA signals and compare the CA signals to the expected variability of an amplitude of an R-wave or presence of an R-wave based and/or compare the CA signals to minimum values for prior corresponding motion data.

In another example, CA signals due to dysrhythmia (e.g. premature ventricular contractions (PVCs) may change the directional depolarization as detected by the sensing hardware and firmware of the IMD 100. For example, PVCs may have a higher R-wave amplitude and a broader QRS morphology that results in a time delay of the subsequent cardiac cycle. In accordance with embodiments herein, the expected variability of the R-wave may remain unchanged based on the occurrence of a single cardiac beat exhibiting dysrhythmia. For example, R-wave amplitude decreases when a patient changes postures from a supine posture, to a right side-laying posture, a left-side laying posture, a sitting posture, and a standing posture. The reduction in R-wave amplitude corresponding to changes in posture present an increased risk for lack of detection of R-waves and/or R-wave variability due to a respiration cycle. In one example, the MDA process 237 detects such postural changes at the physiological sensor 270 and, based thereon, lowers the expected R-wave variability to improve detection of the CA signals. Lowering the expected R-wave variability may reduce or eliminate false brady pause arrhythmia detection.

In one example, the accelerator signatures may be an AC-high frequency component from the 3-D accelerometer. The AC-high frequency component may correspond to one or more axes of the accelerometer and, additionally or alternatively, may represent a composite AC-high frequency component formed from a combination (e.g., a sum) of the AC-high frequency components from the three electrical signals. The composite AC-high frequency component generally represents the acceleration signature that is indicative of motion data produced during a corresponding cardiac cycle due to one or more of the patient posture or the respiration cycle. The AC-high frequency component may include signals having a frequency of 10 KHz or more, and more preferably in the range of 10-100 kHz.

In yet another example, the three directional signals generated by the 3-D accelerometer may be passed through one or more bandpass filters 271 to separate the AC-high frequency component. The output of the bandpass filter 271, including primarily only AC-high frequency components, represents an acceleration signature indicative of motion data produced during a corresponding cardiac cycle due to one or more of the patient posture or the respiration cycle. In one example, the sensor may couple to a bandpass filter 271 for each axis of the accelerometer. In one example, each bandpass filter 271 is the same for each axis, whereas in other examples, each bandpass filter 271 may be different for each axis of the accelerometer. In yet another example, the two bandpass filters may be identical for two axes, and third bandpass filter may be different for a third axis. In an additional or alternative example, in order to detect activity levels, the 3-D accelerometer may include another bandpass filter 271 that may have a different sensitivity setting. In yet another example, each bandpass filter 271 may have two filter settings, with a first filter setting between 7.5-100 Hz and a second filter setting between 15-100 Hz. In such an example, the filter with the 7.5 Hz lower −3 dB is ideal for collecting higher frequency content, whereas the filter with 15 Hz lower −3 dB is a better option in collecting higher frequency content while minimizing low frequency drift, or noise. Therefore, depending on the desired content of the motion data, a different filter, or setting may be utilized.

Specifically, the microcontroller 220 may command the bandpass setting based on operational and patient conditions.

A battery 272 provides operating power to all of the components in the IMD 100. The battery 272 is capable of operating at low current drains for long periods of time. The battery 272 also desirably has a predictable discharge characteristic so that elective replacement time may be detected. As one example, the housing 102 employs lithium/silver vanadium oxide batteries. The battery 272 may afford various periods of longevity (e.g., three years or more of device monitoring). In alternate embodiments, the battery 272 could be rechargeable. See, for example, U.S. Pat. No. 7,294,108, titled "Cardiac event micro-recorder and method for implanting same", which is hereby incorporated by reference.

Figure 3:
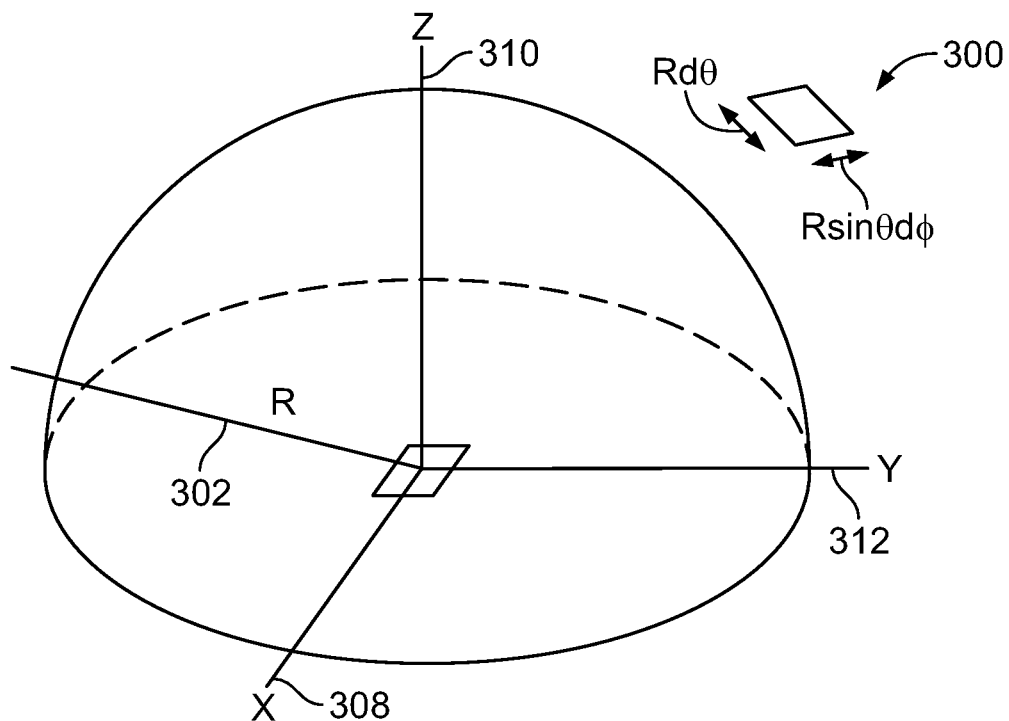
FIG. 3 illustrates force vectors experienced by the IMD in accordance with embodiments herein.

FIG. 3 illustrates force vectors experienced by the IMD 100 as determined by an accelerometer. The microcontroller 220 utilizes device location information, collected from the physiologic sensor 270, or accelerometer, to define a base local device coordinate system 300 for the IMD. The base local device coordinate system 300 may correspond to a global coordinate system and may be defined in terms of various types of coordinate systems, such as a Cartesian coordinate system, Polar coordinate system or otherwise. The microcontroller 220 defines the base local device coordinate system 300 relative to a reference vector 302 that corresponds to and is defined by, the gravitational force of earth. Regardless of the position and orientation of the IMD 100, the gravitational force of earth will remain constant and serve as a reference vector having a fixed magnitude and direction.

During a calibration procedure to calibrate the accelerometer, the accelerometer is orients the IMD 100 to a known posture with respect to the gravitational force. When the patient is at a baseline posture (e.g., a supine baseline posture), the microcontroller 220 collects device location information over a period of time (e.g., 10 second, 1 minute, 5 minutes, etc.) from the physiologic sensor 270, providing location information in the X, Y and Z directions 308, 312, 310, relative to the Earth's gravitational force. The IMD 100 has an initial/reference position and orientation within the base local device coordinate system 300. For example, the initial/reference position and orientation may define an orientation of a longitudinal axis extending through a center of the IMD 100 and may define a position of a reference point on the IMD 100 (e.g., a distal or proximal tip, a center of mass, a center point on a select electrode and the like). The microcontroller 220 determines averages (e.g., rectified averages) to determine baseline motion data. The baseline motion data includes at least one of a baseline supine posture or a baseline respiration cycle. The baseline posture (e.g., the supine baseline posture) is used to determine other postures (e.g., laying on a right side, laying on a left side, sitting, standing, walking, and the like). After the calibration procedure, the calibration acceleration signatures are utilized to determine an axis of the accelerometer associated with a current posture. The confirmation acceleration signatures are obtained along the axis of the accelerometer in connection with the motion data to determine whether the at least one of the posture or respiration cycle at least in part caused the COI to exceed the COI limit. The baseline motion data may be stored in a rolling buffer or a database and provided automatically to the MDA process 237 on a periodic basis, such as upon a postural change or rise in a value of the respiration cycle beyond a specified variation. For example, when an R-wave exceeds an expected variability of an amplitude of an R-wave or a presence of the R-wave, the MDA process 237 compares the motion data to the baseline motion data to identify motion changes that are associated with changes in amplitude of the CA signals that occur with different postures and minute ventilation increase and decrease changes.

Methods for Labeling Arrhythmia

Figure 6A:
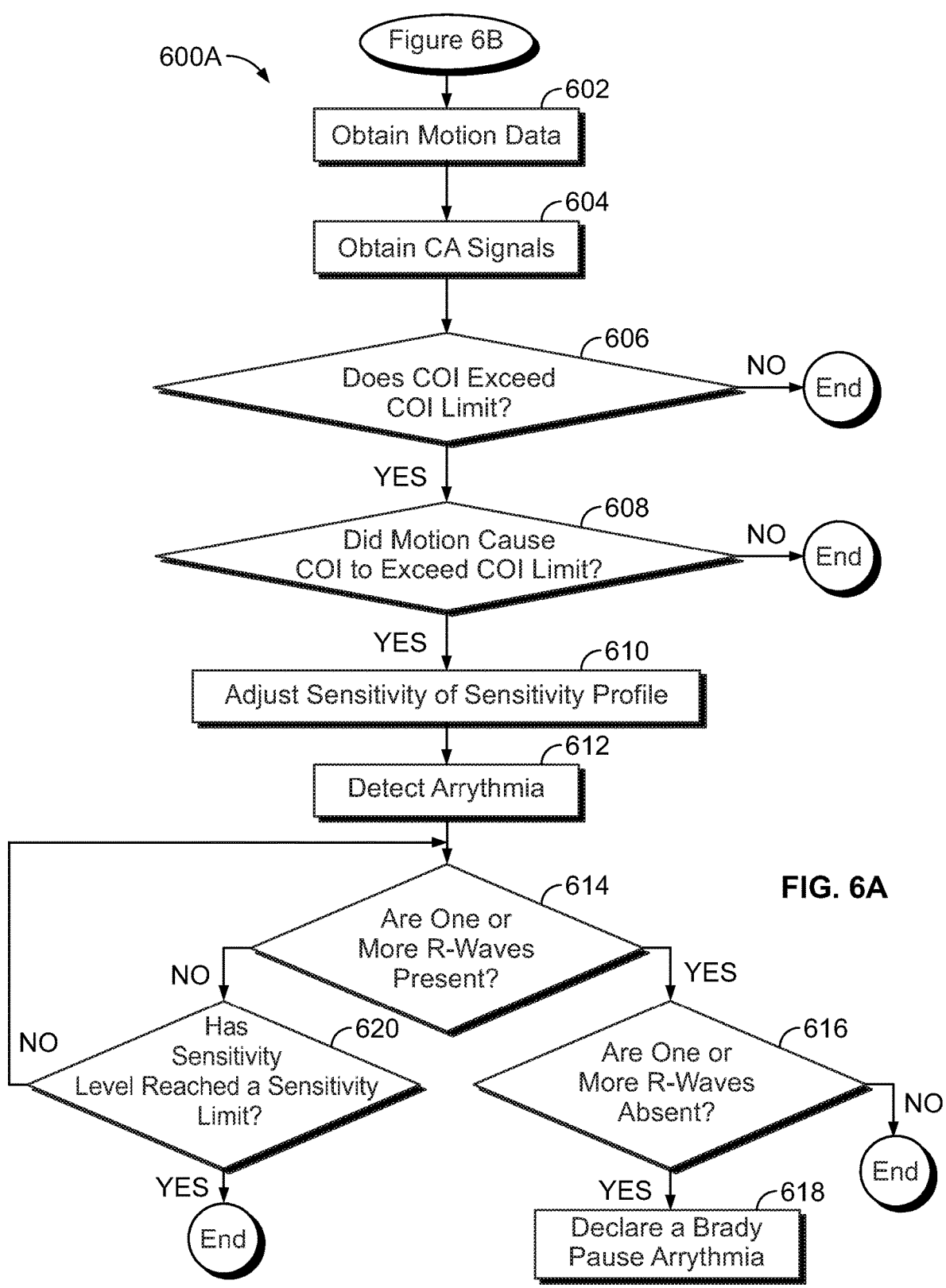
FIG. 6A illustrates a flow block diagram of a method for reducing false declarations of cardiac events due to undersensing or oversensing of R-waves in accordance with embodiments herein.
Figure 6B:
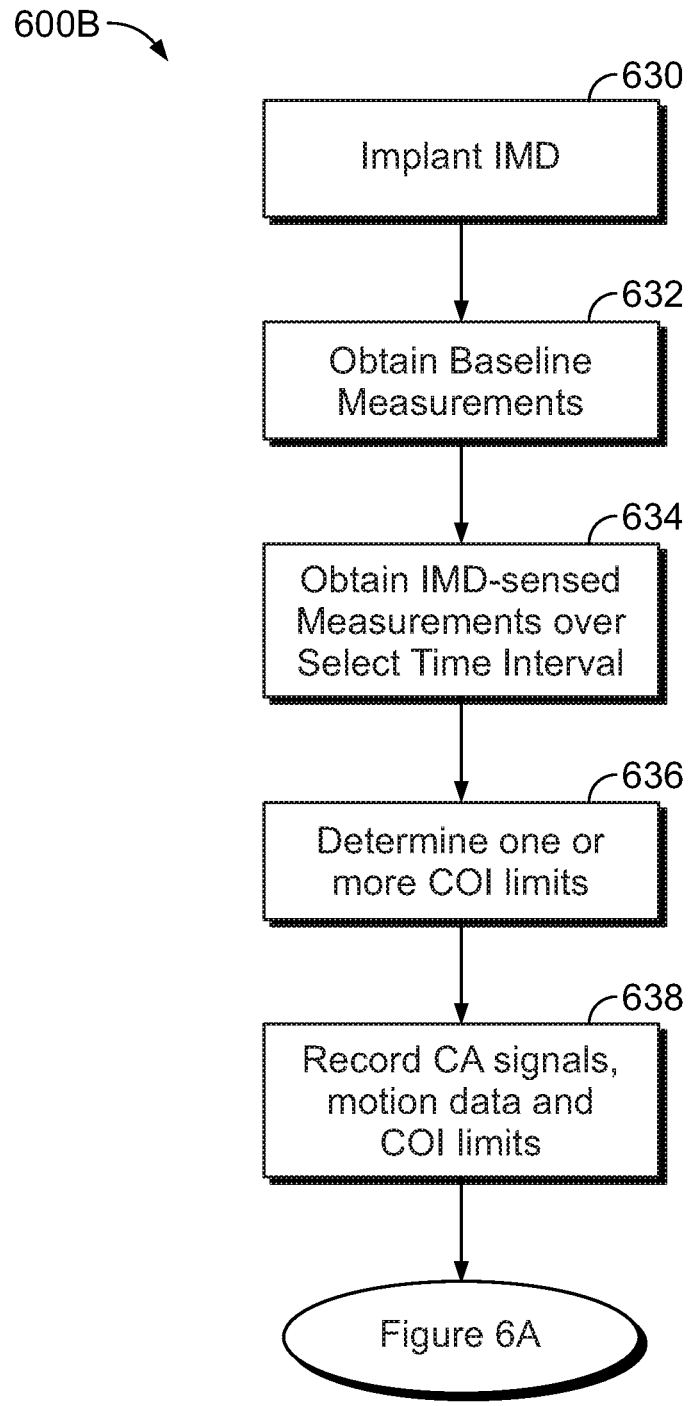
FIG. 6B illustrates a flow block diagram of an example of additional or alternative aspects of the method for reducing false declarations of cardiac events due to undersensing or oversensing of R-waves in accordance with embodiments herein.
Figure 6C:
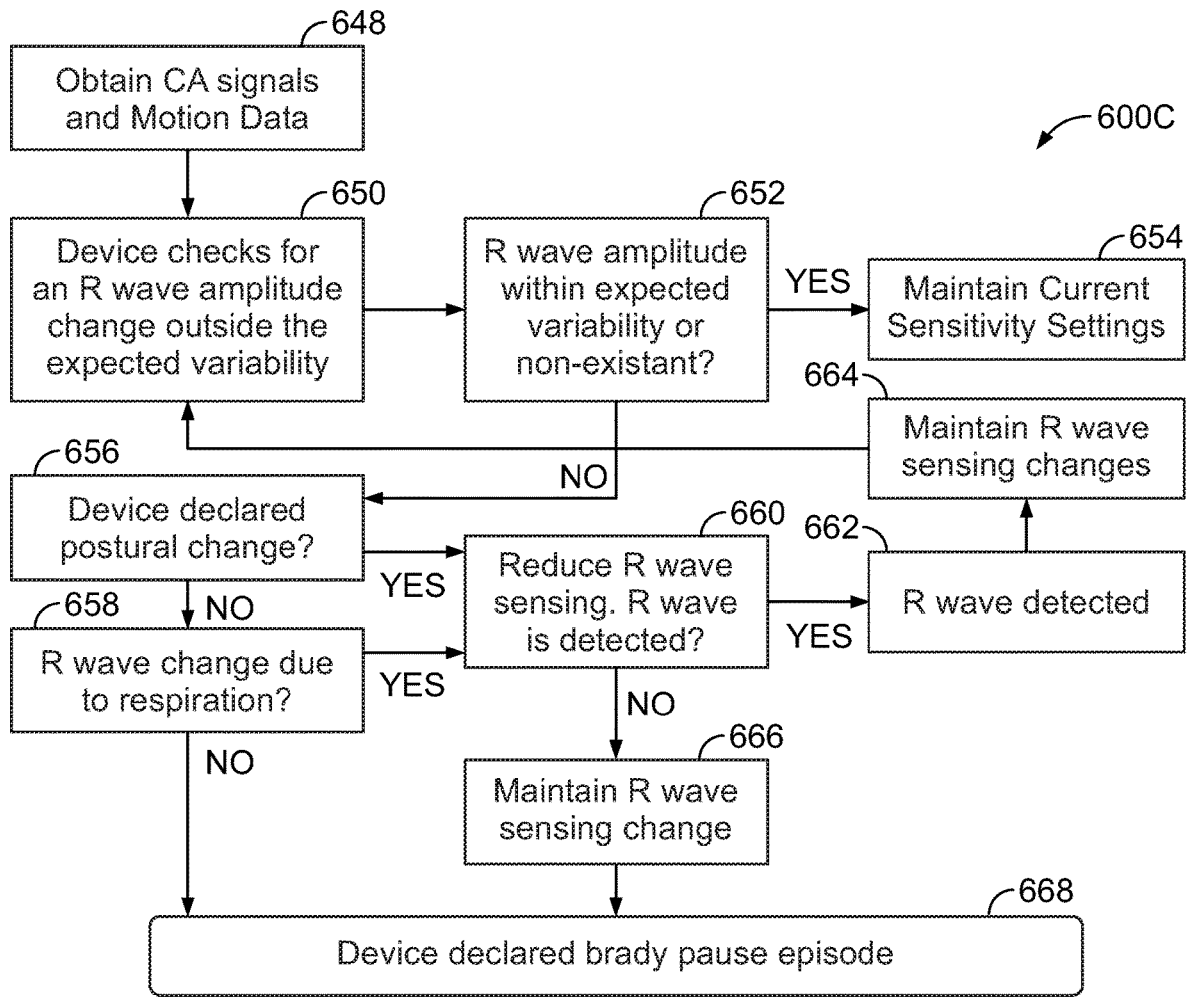
FIG. 6C illustrates a flow block diagram of an example implementation of the method of FIG. 6A in accordance with embodiments herein.

FIGS. 6A-6C illustrate computer-implemented methods 600A-600C for reducing false declarations of arrhythmias due to undersensing or oversensing of R-waves. In one example, the methods 600A-600C are performed utilizing the CA signals and motion data detected and retrieved by the systems and methods described in detail herein. All or a portion of the operations of FIGS. 6A-6C may be implemented by one or more processors of the IMD 100 configured with executable instructions. Portions of the operations of FIGS. 6A-6C may also be implemented by one or more processors of one or more of a local external device and/or a remote server. It should be recognized that while the operations of methods 600A-600C are described in a somewhat serial manner, one or more of the operations of method 600 may be continuous and/or performed in parallel with one another. For example, the various operations of the IMD 100 may be continuous and/or performed in parallel with one another and/or other functions of the IMD 100. Each one of the methods 600A-600C may be performed alone or in combination with one or more of the remaining methods 600A-600C. Also, unless otherwise indicated, each operation of methods 600A-600C is performed under the control of one or more processors configured with program instructions.

Beginning at 602, the one or more processors obtain motion data indicative of at least one of a patient posture or a respiration cycle. The motion data is indicative of at least one of a posture or a respiration cycle. The motion data may be obtained as at least one of an acceleration signature and/or impedance signature. In one example, the one or more processors of the IMD 100 obtain acceleration signatures at a physiological sensor 270 of the IMD 100 that are indicative of motion data generated during the cardiac beats. In one example, the physiological sensor is physiological sensor 270 of FIG. 2A and is an accelerometer. In the example, the one or more processors obtain the acceleration signatures from or about one or more axes, X, Y, or Z, of the accelerometer. In an additional or alternative example, the one or more processors filter the accelerometer signal to obtain a motion component indicative of a respiratory cycle, and obtain the minute ventilation increase and decrease changes of the respiratory cycle. Additionally or alternatively, the one or more processors obtain impedance signatures via the CI sensing circuit 242 that are indicative of motion data generated during cardiac beats. In one example, the one or more processors obtain the impedance signatures indicative of the respiratory components of minute ventilation (e.g., respiratory rate and tidal volume) by measuring the impedance differences generated when the CI sensing circuit 242 sends a constant impedance between electrodes and monitors the return voltage.

The motion data may be for the same series of cardiac beats as the CA signals obtained in operation 604. Additionally or alternatively, the motion data may be for a series of cardiac beats following the cardiac beats for which the CA signals were obtained in operation 604. Optionally, the motion data may be for a series of cardiac beats that include at least some cardiac beats of the series of cardiac beats as the CA signals and cardiac beats following the same series of cardiac beats as the CA signals obtained in operation 604.

At 604, the one or more processors obtain CA signals for a series of cardiac beats. The CA signals include device documented feature markers (e.g., R-wave, R-wave amplitude, and the like) to identify the cardiac beats sensed by the IMD 100 at the electrodes. All device documented feature markers are declared and designated by the IMD 100 utilizing the MDA process 237 to analyze the CA signals.

The operations of FIG. 6A (and FIGS. 6B-6C) may be staged to be performed upon the CA signals and motion data at various times, such as in real time (e.g., during or shortly after a patient experiences an episode) or at any time after storage of the CA signals and motion data. The operations of FIG. 6 may be performed by devices and systems at various proximity to a patient with the IMD 100. For example, the CA signals and motion data may be read out of an IMD 100 and transmitted to a local portable external device (e.g., smartphone, table computer, laptop computer, smartwatch, etc.), where the local portable external device locally implements all or a portion of the operations described in connection with FIG. 6 while in close proximity to the patient. Additionally or alternatively, the CA signals and motion data may be read out of the IMD 100 to a local portable external device and transmitted to a remote server, medical network, physician computer and the like, which implements all or a portion of the operations described in connection with FIG. 6 remote from the patient. Additionally or alternatively, the CA signals and motion data may be read from the IMD 100 by a programmer device, such as during a patient visit to a physician, where the programmer device implements all or a portion of the operations described in connection with FIG. 6 during or after a patient-doctor visit.

At 606, the one or more processors identify whether a CoI from at least a first segment of the CA signals exceeds a COI limit. The one or more processors analyze the CA signals to assess whether the COI exceeded the COI limit. The one or more processors analyze the CA signals to assess one or more of the rate of cardiac beats, the morphology of the QRS complexes, the duration of the QRS complexes, the AR intervals, T-wave morphology, the presence of R-waves, R-wave amplitudes and the like. In one example, the COI limit represents at least one of expected variability of an amplitude of an R-wave or a presence of the R-wave. The MDA process 237 identifies whether the variability of the amplitude of the R-wave or the presence of the R-wave exceeds the expected variability of the amplitude of the R-wave or the presence of the R-wave in at least the first segment of the cardiac beats. Optionally, the one or more processors record an ensemble of cardiac beats and utilize a mathematical operation (e.g., averaging, mean, median, and the like) to combine the CA signals to form resultant CA signals that are analyzed to identify whether the COI exceeds the COI limit.

If the COI does not exceed (or falls below) the COI limit, the process interprets the condition to confirm the current sensitivity setting. By confirming the current sensitivity setting, the process declares that R-waves are neither undersensed or oversensed by the IMD 100, and the process ends. For example, if the expected variability of the amplitude of the R-wave does not exceed (or falls below) the corresponding COI limit, the process declares that there is no undersensing or oversensing of R-waves by the IMD 100.

If the COI exceeds the COI limit, the process interprets the condition to confirm that R-waves may be oversensed or undersensed by the IMD 100 due to changes in the at least one of the posture or the respiration cycle, and the process proceeds to 608. For example, if the expected variability of the amplitude of the R-wave exceeds the COI limit, the process indicates that there may be undersensing or oversensing of R-waves by the IMD 100 due to the at least one or the posture or the respiration cycle that may result in false arrhythmia detection. Stated differently, the process indicates that the sensitivity of the sensing profile of the CA sensing parameter may need adjustment because the R-waves may be undersensed or oversensed due to at least one of the posture or the respiration cycle. Upon identifying that the COI exceeds the COI limit, the process declares that the COI exceeds the COI limit.

At 608, the one or more processors analyze the motion data to determine whether at least one of the posture or the respiration cycle at least in part caused the COI to exceed the COI limit. The analyzing operation includes comparing the motion data to baseline motion data. The baseline motion data may be indicative of at least one of a supine baseline posture or a baseline respiration cycle. The comparing operation includes identifying motion changes that are associated with changes in an amplitude of the CA signals that occur with different postures and minute ventilation increase and decrease changes. For example, the MDA process 237 may identify whether the variability of the amplitude of the R-wave exceeds, e.g., a select value of standard deviations (e.g., 2 standard deviations) based on the expected R-wave amplitude for the posture for the patient (e.g., based on previously collected motion data) and/or the expected R-wave amplitudes (e.g., R-wave amplitudes exhibited by relevant patient populations).

In one example, the motion data is indicative of the posture and the determining operation includes determining that the motion data is indicative of a posture change that reduced an amplitude of the CA signals by an amount sufficient to cause the COI to exceed the COI limit. In the example, the determining operation includes determining that the posture change is a type of posture change that reduces an amplitude of R-waves in the CA signals by an amount sufficient to prevent detection thereof based on a sensing profile. For example, the motion data is indicative of a change in posture from a supine position to a right-side laying position. The supine posture has an expected value of R-wave amplitude that is greater than (e.g., twice) the expected value of R-wave amplitude for the right-side laying posture.

In an additional or alternative example, the motion data is indicative of the respiration cycle and the determining includes determining that the respiration cycle reduced an amplitude of the CA signals by an amount sufficient to cause the COI to exceed the COI limit. In the example, the determining operation includes determining that the change in respiration cycle during a first posture (e.g. a supine posture) to a second posture (e.g., a right-side laying posture) is a type of change in respiration cycle that reduces an amplitude of R-waves in the CA signals by an amount sufficient to prevent detection thereof based on a sensing profile. For example, the respiration cycle during the supine posture has an expected value of R-wave amplitude that is greater than (e.g., twice) the expected value of R-wave amplitude for the respiration cycle during the right-side laying posture.

Based on determining that at least one of the posture or the respiration cycle did not reduce the amplitude of the CA signals by an amount sufficient to cause the COI to exceed the COI limit, the process interprets the condition to confirm the current sensitivity setting. Stated differently, the process indicates that the sensitivity of the sensing profile of the CA sensing parameter does not need adjustment because the R-waves are not undersensed or oversensed. By confirming the current sensitivity setting, the process declares that R-waves are neither undersensed or oversensed by the IMD 100 due to at least one of the posture or the respiration cycle, and the process ends.

Based on determining that at least one of the posture or the respiration cycle did, at least in part, reduce the amplitude of the CA signals by an amount sufficient to cause the COI to exceed the COI limit, the process interprets the condition to confirm that at least one of the posture or the respiration cycle did cause the COI to exceed the COI limit. Stated differently, the process indicates that the sensitivity of the sensing profile of the CA sensing parameter needs adjustment because the R-waves are undersensed or oversensed. By confirming that at least one of the posture or the respiration cycle did, at least in part, cause the COI to exceed the COI limit, the process declares that R-waves are undersensed or oversensed by the IMD 100 due to at least one of the posture or the respiration cycle, and the process proceeds to 610.

At 610, the one or more processors automatically adjust the CA sensing parameter utilized by the IMD 100 to detect R-waves in subsequent CA signals. The CA sensing parameter defines a sensitivity profile. The adjusting operation includes adjusting the CA sensing parameter to change the sensitivity of the sensitivity profile to at least reduce false arrhythmia detection due to undersensing or oversensing R-waves. For example, when motion data is determined to cause the COI to exceed the COI limit, the processors may declare the sensitivity profile adjustment to be an increase or decrease in the COI (e.g., R-wave, R-wave amplitude) detection threshold. As another example, the processors may declare the sensitivity profile adjustment to be an increase in the R-wave detection threshold when P-waves are identified as R-waves due to changes in the CA signals induced, at least in part, by at least one of the posture and the respiration cycle. As another example, the processors may declare the sensitivity profile adjustment to be an increase in the decay delay value when T-waves are designated to be R-waves due to changes in the CA signals induced, at least in part, by at least one of the posture and the respiration cycle. The change in sensitivity (or the updated sensitivity) of the sensitivity profile may be saved in, e.g., a confirmation log. Once the one or more processors adjust the sensitivity of the sensitivity profile, flow moves to 612.

The increase or decrease in the sensitivity of the sensitivity profile adjustment may be a predefined step (e.g., increase threshold by X mV or Y %). Optionally, the increase or decrease may be based on an extent or nature of the changes in the CA signals induced, at least in part, by at least one of the posture and the respiration cycle. For example, when the MDA process 237 indicates that the at least one of the posture or the respiration cycle reduced the presence of R-waves or the amplitude of R-waves by a relatively large factor (e.g., as compared to the baseline motion data), the process may decrease the R-wave detection threshold by a larger factor as compared to when the MDA process indicates that the at least one of the posture or the respiration cycle reduced the presence of R waves or the amplitude of R-waves by a relatively small factor. As another example, a decay delay value adjustment and/or refractory period value adjustment may be determined may be based on an extent or nature of the changes in the CA signals induced, at least in part, by at least one of the posture and the respiration cycle.

Optionally, the one or more processors may identify additional or alternative sensitivity profile adjustments based on a database of sensitivity profile settings that are correlated to CA signals and motion data for a patient population. For example, a database may be maintained of CA signals and motion data for various postures and/or activity levels, where the CA signals and motion data are correlated with sensitivity profile settings that are used by the IMD 100 to collect the CA signals and motion data. The patient population database may also indicate which sensitivity profile settings achieved desired results and which sensitivity profile settings did not achieve desired results. The database may further include quality indicators indicative of whether the sensitivity profile settings were deemed to collect good or accurate results (e.g., correctly sense R-waves without over-sensing P-waves or T waves, and correctly sense all R-waves without undersensing of R-waves with smaller amplitude). The database may further include quality indicators indicative of whether the sensitivity profile settings were deemed to accurately declare arrhythmia detection in a high percentage of the instances of arrhythmias. The quality indicators may be automatically entered based on automated analysis of the data within the database and/or entered by physicians or other medical personnel as sensitivity profile settings are adjusted and/or calibrated for individual patients. The database may be available on a medical network, through a cloud computing service and/or other local or remote source.

At 612, the one or more processors detect an arrhythmia based on a presence or absence of one or more of the R-waves in at least a second segment of the CA signals. Based on detecting an arrhythmia utilizing the current sensitivity for the sensitivity profile, arrhythmia detection is improved. Arrhythmia detection is improved by at least reducing undersensing or oversensing of R-waves due to, at least in part, at least one of a posture or a respiration cycle or changes therein.

At 614, the one or more processors compare the subsequent CA signals to a current sensitivity level to determine whether one or more R-waves are present within the subsequent CA signals. Based on the process determining that one or more R-waves are present within the subsequent CA signals, the process interprets the condition to represent a candidate brady pause arrhythmia and flow moves to 616.

At 616, the one or more processors detect the absence of one or more of the R-waves from the subsequent CA signals. If the process determines that one or more of the R-waves are not absent from the subsequent CA signals, the process interprets the condition to not represent a brady pause arrhythmia and the process ends. If the process determines that one or more of the R-waves are absent from the subsequent CA signals, the process interprets the condition to represent a brady pause arrhythmia, and flow moves to 618.

At 618, the one or more processors declare a brady pause arrhythmia. Optionally, based on declaring a brady pause arrhythmia, the one or more processors may deliver or withhold an arrhythmia treatment for treating a brady pause arrhythmia, store the CA signals declared a brady pause arrhythmia (e.g., as an electrogram), and/or generate an alert and/or event marker communicating the declaring of a brady pause arrhythmia.

Returning to 614, based on the process determining that one or more R-waves are not present within the subsequent CA signals, the process interprets the condition as indicating potential undersensing of the CA signals (e.g., R-waves) and flow moves to 620.

At 620, the one or more processors determine if the current sensitivity level has reached the sensitivity limit 218. Based on the one or more processors determining that the current sensitivity level has not reached the sensitivity limit 218, the process adjusts the sensitivity of the sensitivity profile and flow returns to 614. The process repeats the comparing operation while progressively adjusting the current sensitivity level until the one or more R-waves are detected in a beat segment of interest in the CA signals and/or the current sensitivity level reaches a sensitivity limit. Based on the one or more processors determining that the current sensitivity level has reached the sensitivity limit 218, the process interprets the condition to represent a noise and/or LOC condition, and the process ends.

FIG. 6B illustrates a flow block diagram of an example of additional or alternative aspects of the method for reducing false declarations of cardiac events due to undersensing or oversensing of R-waves in accordance with embodiments herein. FIG. 6B illustrates aspects of implanting and calibrating the IMD 100.

At 630, the IMD 100 is implanted during an implant procedure. In at least some embodiments, the IMD 100 is configured to be placed subcutaneously utilizing a minimally invasive approach. The IMD 100 may be configured to be activated by the patient or clinician or automatically activated, in connection with recording subcutaneous ECG signals.

At 632, the one or more processors obtain baseline measurements of the CA signals and motion data. Obtaining baseline measurements of the CA signals may include obtaining baseline measurements of the patient's P-wave and QRS parameters and motion data. The baseline motion data may include baseline accelerometer signatures indicative of posture and/or the respiration cycle. Additionally or alternatively, the motion data may include baseline impedance signatures indicative of the respiration cycle. Once baseline measurements are obtained, flow moves to 634.

At 634 and 636, the one or more processors obtain additional measurements (e.g., additional baseline measurements and/or calibration measurements) of the CA signals and motion data over a select time interval and determine one or more COI limits. For example, the one or more processors obtain IMD-measured supine posture and P-wave, R-wave, and QRS measurements over the select time interval (e.g., 5 s, 10 s, 1 min, 5 min, and the like). In a further example, CA signals and motion data corresponding to the supine posture for the physiological sensor 270 (e.g., the accelerometer) may be obtained and the variation in the P-wave, R-wave, and QRS measurements over a plurality of respiration cycles analyzed to determine one or more COI limits. In an additional or alternative example, CA signals and motion data corresponding to the supine posture for the CI sensing circuit 242 may be obtained and the variation in the P-wave, R-wave, and QRS measurements over a plurality of respiration cycles analyzed to determine one or more COI limits. In one example, one or more COI limits may be determined by measuring variation in the P-wave, R-wave, and QRS measurements over a plurality of respiration cycles during the supine posture to establish, as the one or more COI limits, one or more standard deviations of the associated amplitudes of the CA signals for the supine and, optionally, additional postures.

At 638, the one or more processors record the CA signals, motion data, and one or more COI limits for subsequent use and flow moves to operation 602 of FIG. 6A.

FIG. 6C illustrates a flow block diagram of an example implementation of the method of FIG. 6A in accordance with embodiments herein. Beginning at operation 648, the one or more processors obtain CA signals and motion data indicative of at least one of a patient posture or a respiration cycle in accordance with operations 602-604 of FIG. 6A.

At 652, the one or more processors determine whether the R-wave amplitude variability, as the COI, is within the expected variability or if the R-wave is absent in accordance with operation 606 of FIG. 6A. Based on determining that the R-wave amplitude variability is within the expected R-wave amplitude variability, flow moves to 654. At 654, the one or more processors maintain the sensitivity of the sensitivity profile.

At 652, based on determining that the R-wave is absent, flow moves to 656. At 656, the one or more processors analyze the motion data to determine whether the posture (or change in posture) at least in part caused the R-wave amplitude variability to exceed the expected R-wave amplitude variability in accordance with operation 608 of FIG. 6A. Based on determining that the posture (or change in posture) at least in part caused the R-wave amplitude variability to exceed the expected R-wave amplitude variability, the one or more processors declare a change in posture at least in part caused the R-wave amplitude variability to exceed the expected R-wave amplitude variability and flow moves to 660.

At 660, the one or more processors reduce the sensitivity of the sensitivity profile and analyze the CA signals to determine whether an R-wave is detected at the current sensitivity. Based on detecting an R-wave, flow moves to 662. At 662, the one or more processors declare an R-wave and flow moves to 664. At 664, the one or more processors maintain the current sensitivity of the sensitivity profile and flow returns to 648 and/or 650.

Returning to operation 656, based on determining that the posture (or change in posture) at least in part caused the R-wave amplitude variability to exceed the expected R-wave amplitude variability, the one or more processors declare a change in posture and flow moves to 660. At 660, the one or more processors analyze the motion data to determine whether the respiration cycle at least in part caused the R-wave amplitude variability to exceed the expected R-wave amplitude variability in accordance with operation 608 of FIG. 6A. Based on determining that the respiration cycle at least in part caused the R-wave amplitude variability to exceed the expected R-wave amplitude variability, the one or more processors declare the respiration cycle at least in part caused the R-wave amplitude variability to exceed the expected R-wave amplitude variability and flow moves to 660.

At 660, as described above, the one or more processors reduce the sensitivity of the sensitivity profile and analyze the CA signals to determine whether an R-wave is detected at the current sensitivity. Based on detecting an R-wave, flow moves to 662. At 662, the one or more processors declare an R-wave and flow moves to 664. At 664, the one or more processors maintain the current sensitivity of the sensitivity profile and flow returns to 648 and/or 650.

Returning to 660, based on determining that the respiration cycle did not cause the R-wave amplitude variability to exceed the expected R-wave amplitude variability, the one or more processors declare the respiration cycle did not cause the R-wave amplitude variability to exceed the expected R-wave amplitude variability and flow moves to 666. At 666, the one or more processors maintain the current sensitivity of the sensitivity profile and flow moves to 668. At 668, the one or more processors declare a brady pause arrhythmia in accordance with operation 618 of FIG. 6A.

Returning to 658, based on determining that the respiration cycle did not cause the R-wave amplitude variability to exceed the expected R-wave amplitude variability, the one or more processors declare the respiration cycle did not cause the R-wave amplitude variability to exceed the expected R-wave amplitude variability and flow moves to 668. At 668, the one or more processors declare a brady pause arrhythmia in accordance with operation 618 of FIG. 6A.

Figure 7:
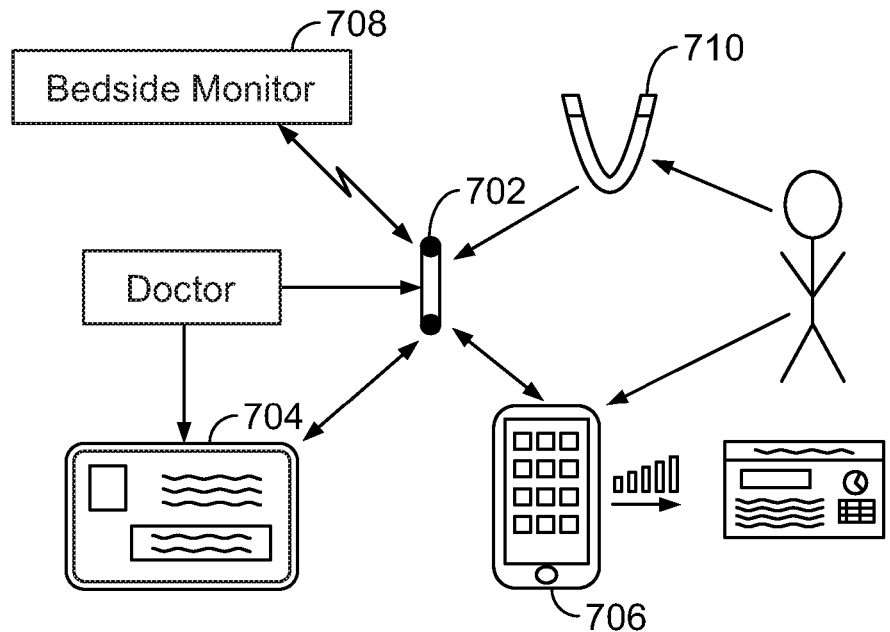
FIG. 7 illustrates a system level diagram indicating potential devices and networks in which the methods and systems herein may be utilized in accordance with embodiments herein.

FIG. 7 illustrates a system level diagram indicating potential devices and networks that utilize the methods and systems herein. For example, an IMD 702 (e.g., IMD 100 of FIG. 1) may be utilized to collect a CA data set. The IMD 702 may supply the CA data set (CA signals, sensitivity levels, and motion data) to various local external devices, such as a tablet device 704, a smart phone 706, a bedside monitoring device 708, a smart watch and the like. The devices 704-708 include a display to present the various types of the CA signals, markers, statistics, diagnostics and other information described herein. The IMD 702 may convey the CA data set over various types of wireless communications links to the devices 704, 706 and 708. The IMD 702 may utilize various communications protocols and be activated in various manners, such as through a Bluetooth, Bluetooth low energy, Wi-Fi or other wireless protocol. Additionally or alternatively, when a magnetic device 710 is held next to the patient, the magnetic field from the device 710 may activate the IMD 702 to transmit the CA data set and arrhythmia data to one or more of the devices 704-708.

The processes described herein for reducing false declarations of cardiac events due to undersensing or oversensing of R-waves may be implemented on one or more of the devices 704-708. Additionally or alternatively, the IMD 702 may also for reducing false declarations of cardiac events due to undersensing or oversensing of R-waves may be implemented on one or more of the devices. The devices 704-708 may present the CA signals and motion data to clinicians in various manners. As one example, arrhythmia markers may be illustrated on EGM signal traces. Arrhythmia and sinus markers may be presented in a marker channel that is temporally aligned with original or modified CA signals and motion data. Additionally or alternatively, the duration and heart rate under arrhythmia may be formatted into histograms or other types of charts to be presented alone or in combination with CA signals and motion data.

Figure 8:
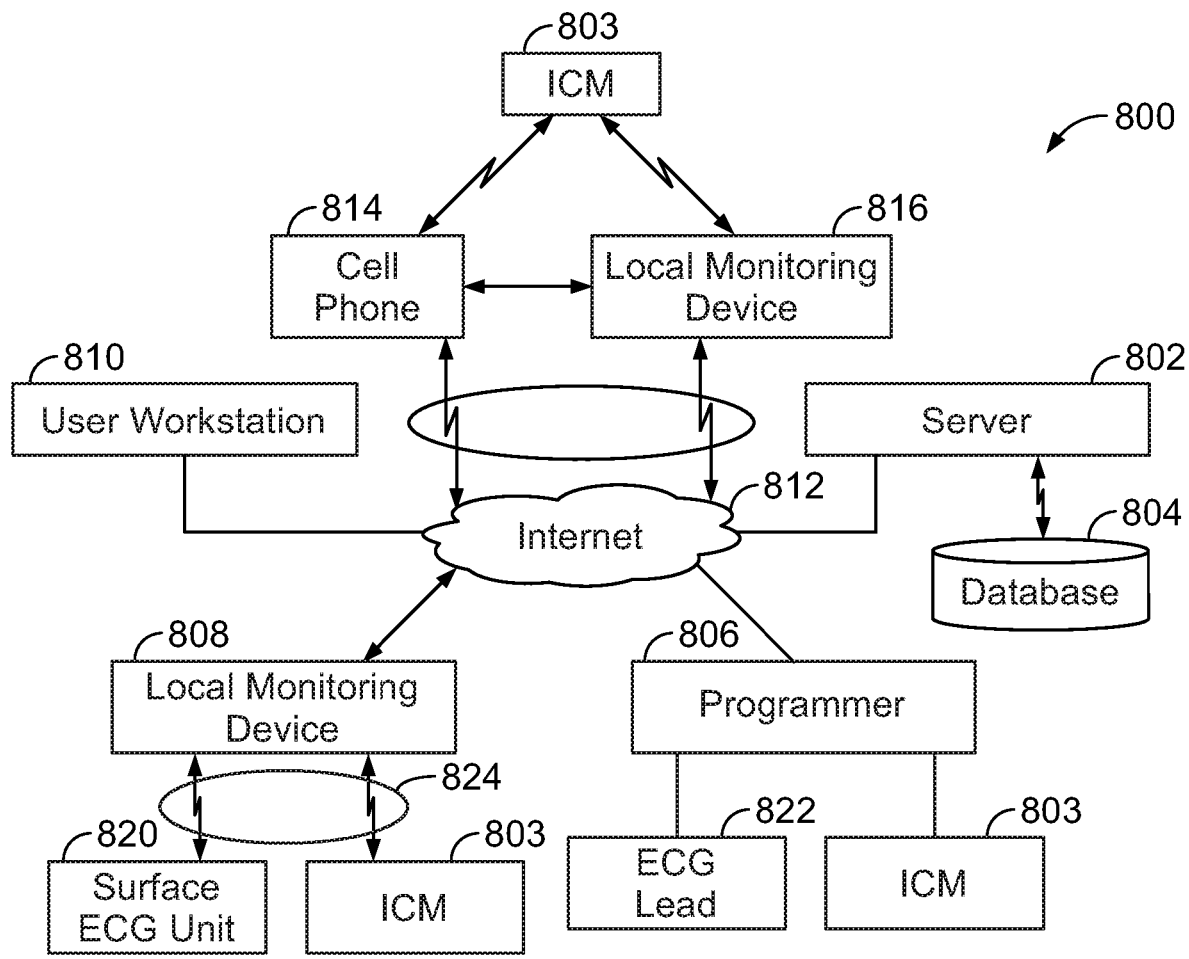
FIG. 8 illustrates a distributed processing system in accordance with embodiments herein.

FIG. 8 illustrates a distributed processing system 800 in accordance with embodiments herein. The distributed processing system 800 includes a server 802 connected to a database 804, a programmer 806, a local monitoring device 808 (e.g., IMD 100) and a user workstation 810 electrically connected to a network 812. Any of the processor-based components in FIG. 6 (e.g., workstation 810, cell phone 814, local monitoring device 816, server 802, programmer 806) may perform the processes discussed herein.

The network 812 may provide cloud-based services over the internet, a voice over IP (VoIP) gateway, a local plain old telephone service (POTS), a public switched telephone network (PSTN), a cellular phone-based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 802 is a computer system that provides services to the other computing devices on the network 812. The server 802 controls the communication of information such as CA signals, motion data, bradycardia episode information, asystole episode information, arrhythmia episode information, markers, CA signal waveforms, heart rates, and device settings. The server 802 interfaces with the network 812 to transfer information between the programmer 806, local monitoring devices 808, 816, user workstation 810, cell phone 814 and database 804. The database 804 stores information such as CA data, arrhythmia episode information, arrhythmia statistics, diagnostics, markers, CA signal waveforms, heart rates, device settings, and the like, for a patient population. The information is downloaded into the database 804 via the server 802 or, alternatively, the information is uploaded to the server 802 from the database 804. The programmer 806 may reside in a patient's home, a hospital, or a physician's office. The programmer 806 may wirelessly communicate with the IMD 803 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 806 to the IMD 803. The programmer 806 is able to acquire ECG 822 from surface electrodes on a person (e.g., ECGs), electrograms (e.g., EGM) signals from the IMD 803, and/or CA data, arrhythmia episode information, arrhythmia statistics, diagnostics, markers, CA signal waveforms, atrial heart rates, device settings from the IMD 803. The programmer 806 interfaces with the network 812, either via the internet, to upload the information acquired from the surface ECG unit 820, or the IMD 803 to the server 802.

The local monitoring device 808 interfaces with the communication system to upload to the server 802 one or more of the CA signals, motion data, arrhythmia episode information, arrhythmia statistics, diagnostics, markers, CA signal waveforms, heart rates, sensitivity profile parameter settings and detection thresholds. In one embodiment, the surface ECG unit 820 and the IMD 803 have a bi-directional connection 824 with the local RF monitoring device 808 via a wireless connection. The local monitoring device 808 is able to acquire CA signals from the surface of a person, CA data sets and other information from the IMD 803, and/or CA signal waveforms, heart rates, and device settings from the IMD 803. On the other hand, the local monitoring device 808 may download the data and information discussed herein from the database 804 to the surface ECG unit 820 or the IMD 803.

The user workstation 810 may be utilized by a physician or medical personnel to interface with the network 812 to download CA signals, motion data, and other information discussed herein from the database 804, from the local monitoring devices 808, 816, from the IMD 803 or otherwise. Once downloaded, the user workstation 810 may process the CA signals and motion data in accordance with one or more of the operations described above. The user workstation 810 may upload/push settings (e.g., sensitivity profile parameter settings), IMD instructions, other information and notifications to the cell phone 814, local monitoring devices 808, 816, programmer 806, server 802 and/or IMD 803. For example, the user workstation 810 may provide instructions to the IMD 803 in order to update sensitivity profile parameter settings when the IMD 803 determines that the motion data is indicative of at least one of a posture change or a respiration cycle that reduced the amplitude of the CA signals by an amount sufficient to cause the COI to exceed the COI limit.

The processes described herein in connection with reducing false declarations of cardiac events due to undersensing or oversensing of R-waves may be performed by one or more of the devices illustrated in FIG. 8, including but not limited to the IMD 803, programmer 806, local monitoring devices 808, 816, user workstation 810, cell phone 814, and server 802. The process described herein may be distributed between the devices of FIG. 8.

Figure 9:
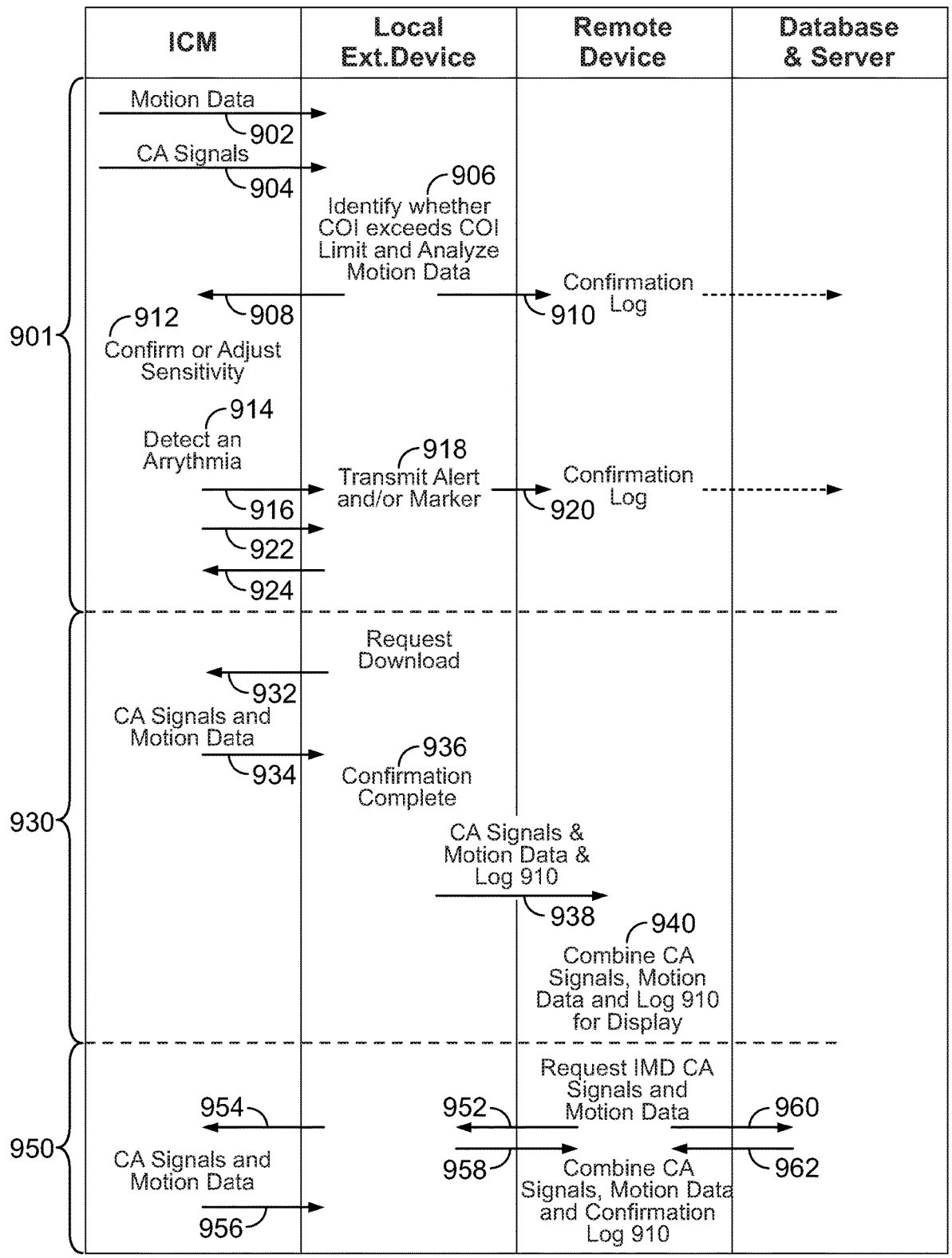
FIG. 9 illustrates a collection of communications between the IMD, a local device, a remote device and a server/database in accordance with embodiments herein.

FIG. 9 illustrates examples of communication sessions between the IMD 100, a local external device, a remote device and a server/database in accordance with embodiments herein. For convenience, reference is made to the devices of FIGS. 7 and 8, in connection with FIG. 9. For example, the local device may represent a cell phone 814, smart phone 706, bedside monitor 708 or local monitoring device 808, 816, while the remote device may represent a workstation 810, programmer 806, or tablet device 704.

During a session for adaptively managing the sensitivity of the sensitivity profile to reduce false declarations of cardiac events 901, at 902, the IMD 100 provides motion data to a local external device. At 904, the IMD 100 provides CA signals to the local external device. At 906, the local external device utilizes the MDA process 237 to identify whether a COI from a first data segment of the CA signals exceeds a COI limit and, based thereon, analyze the motion data to determine whether at least one of the posture or the respiration cycle at least in part caused the COI to exceed the COI limit.

At 908, the local external device returns the results of the identifying and analyzing steps to the IMD. Based on one or more of the COI falling below the COI limit or at least one of the posture or the respiration cycle falling below a level that causes, at least in part, the COI to exceed the COI limit, the local external device transmits confirmation of the current sensitivity level to the IMD 100. Based on the COI exceeding the COI limit and at least one of the posture or the respiration cycle exceeding a level that causes, at least in part, the COI to exceed the COI limit, the local external device communicates a need to adjust the sensitivity of the sensitivity profile to the IMD 100.

In certain instances, it may be desirable to document the results of the identifying and analyzing steps in a confirmation log. The confirmation log may include CA signals, motion data, event markers, and the like. At 910, the remote external device transmits the confirmation log to the remote device and, optionally, the database/server.

At 912, the IMD 100 either confirms or automatically adjusts the CA sensing parameter utilized by the IMD 100 to detect R-waves in subsequent CA signals. The IMD 100 automatically adjusts the CA sensing parameter by changing a sensitivity of a sensing profile of the CA sensing parameter to at least reduce false detections of arrhythmias in subsequent CA signals.

At 914, the IMD 100 detects an arrhythmia based on the presence or absence of one or more of the R-waves in at least a second segment of the CA signals. At 916, based on detecting the absence of one or more of the R-waves in at least the second segment of the CA signals, the IMD declares a brady pause arrhythmia and transmits the declaration to the local external device. At 918, the local external device generates and, optionally, transmits an alert and/or event marker based on the declaration to the remote device and, optionally the database/server. At 920, the local external device updates the conformation log 910. The confirmation log may include CA signals, motion data, event markers, and the like.

Additionally or alternatively, at 922, based on the IMD 100 failing to detect R-waves in at least the second segment of the CA signals, the IMD transmits a query to the local external device regarding whether the current sensitivity level has reached the sensitivity limit. The local external device determines whether the current sensitivity level has reached the sensitivity limit. Based on the determine, the local external device transmits an instruction to the IMD 100. At 924, if the sensitivity limit has not been reached, the local external device transmits an instruction to the IMD 100 to adjust the sensitivity of the sensitivity profile and detect the absence or presence of one or more R-waves in the CA signals. Alternatively, if the sensitivity limit has been reached, the local external device determines that noise and/or an LOC condition exits and transmits an instruction to the IMD 100 to cease obtaining CA signals.

Optionally, a remote pairing session 930 may be performed between CA signals, sensitivity levels, and motion data on an IMD 100 and locally externally stored confirmation logs. For example, the local external device may be directed to initiate a data transfer/download from the IMD 100, such as at 932, at a point in time separate from and after performing the processes described herein for reducing false detections of arrhythmias due to undersensing or oversensing of R-waves. The local external device receives the CA signals, sensitivity levels, and motion data at 934 and determines, at 936, that the CA signals, sensitivity levels, and motion data have already been analyzed to confirm the sensitivity profile and/or confirm arrhythmia detection. At 938, the local external device identifies a confirmation log 910 stored at the local external device that corresponds to the CA signals, sensitivity levels, and motion data, and, at 940, appends the confirmation log 910 to the associated CA signals, sensitivity levels, and motion data, such as based on time of data acquisition. The cumulative information of the CA signals, sensitivity levels, and motion data and confirmation log 910 are transferred, through the external device, to a remote server 802, database 804, workstation 810, programmer 806 or otherwise.

By maintaining the confirmation log, for a particular CA signals, sensitivity levels, and motion data at the local external device in association with the original CA signals, sensitivity levels, and motion data, remote devices (e.g., programmer 806, server 802, etc.) receive and process both the original CA signals, sensitivity levels, and motion data and the confirmation log. The remote device obtains the "traditional" device diagnostic sections, and is also afforded additional information from the confirmation log and is able to account (at 918) for further cumulative adjustments/adjudications in arrhythmia detection before displaying a consolidated set of arrhythmia statistics and diagnostics to a physician or medical personnel.

Additionally or alternatively, the operations of FIG. 9 may be implemented in connection with remotely stored confirmation logs, such as in communication sessions 950. At 952, a remote device may request CA data from a particular IMD 100 by conveying a corresponding request to a local external device associated with the corresponding IMD 100. The local external device forwards the data request, at 954, to the IMD 100, in response thereto, at 956, the IMD 100 transmits the CA signals, sensitivity levels, and motion data to the local external device. The local external device forwards the CA signals, sensitivity levels, and motion data, at 958, to the remote device. Optionally, before relaying the CA signals, sensitivity levels, and motion data, at 958, the local external device may first determine whether the CA signals, sensitivity levels, and motion data have first been analyzed for arrhythmia detection confirmation. In the example at 960, it is presumed that the CA signals, sensitivity levels, and motion data have already been analyzed for arrhythmia detection confirmation and thus the local external device need not perform the confirmation analysis at this time.

Additionally or alternatively, the remote device may include, in the request, a direction to the local external device to not perform arrhythmia detection confirmation (e.g., the remote device knows that in arrhythmia detection confirmation has already been performed and stored elsewhere).

In connection with or separate from the request for CA signals, sensitivity levels, and motion data at 952, the remote device conveys a request, at 960, to a server and database for any confirmation logs related to the requested CA signals, sensitivity levels, and motion data. The request may be broadcast to multiple external devices on the network or directed to a particular server/database known to maintain information in connection with the particular IMD 100. Additionally or alternatively, the remote device may hold the request, at 960, until after receiving the CA signals, sensitivity levels, and motion data, at 958. For example, once a remote device receives the CA signals, sensitivity levels, and motion data, at 958, the remote device may include, within the request for confirmation logs, an indication of the time and date at which the CA signals, sensitivity levels, and motion data were collected. In response to the request, the server and database return, at 962, one or more confirmation logs (if present). Thereafter, the remote device combines the CA signals, sensitivity levels, and motion data and confirmation log 910 to present a consolidated summary of the data to a physician or other medical personnel.

In connection with embodiments herein, the cloud-based approach allows an arrhythmia episode that is detected by the IMD 100 using the traditional detection algorithms in connection with the processes herein for reducing false declarations of arrhythmias due to oversensing or undersensing of R-waves, to be passed through the local external device and stored at the server 802, database 804, workstation 810 or at another remote device within the cloud-based system. When an individual IMD 100 is interrogated for a CA signals and motion data, the interrogation device would also request, from the cloud-based system, any additional information, such as any confirmation logs stored elsewhere within the system. For example, when an external device, such as a cell phone 814, local monitoring device 808, 816 and/or programmer 806 interrogate an individual IMD 100, the cell phone 814, local monitoring device 808, 816 and/or programmer 806 would also broadcast an IMD 100 data supplement request over the cloud-based system. The IMD 100 data supplement request requests additional data/information related to the individual IMD 100 (e.g., based on the IMD 100 serial number). In response thereto, the server 802 and/or other remote system may provide, to the requesting device, one or more confirmation logs or other information regarding past operation of the IMD 100. The requesting device may combine the CA signals, sensitivity levels, and motion data from the IMD 100 with related data (e.g., a confirmation log associated with a particular arrhythmia episode and/or group of cardiac events) from an external source. The external devices pulls data from the cloud in connection with IMD 100 interrogation, and combine the CA signals, sensitivity levels, and motion data from the IMD 100 with any corrective or confirmation data from the log, before presenting a consolidated data summary to a physician or medical personnel.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A computer implemented method, comprising:
under control of one or more processors of a medical device, where the one or more processors are configured with specific executable instructions,
obtaining motion data indicative of at least one of a posture or a respiration cycle;
obtaining cardiac activity (CA) signals for a series of beats;
identifying whether a characteristic of interest (COI) from at least a first segment of the CA signals exceeds a COI limit;
analyzing the motion data to determine whether at least one of the posture or the respiration cycle at least in part caused the COI to exceed the COI limit;
based on the analyzing operation, automatically adjusting a CA sensing parameter utilized by the medical device to detect R-waves in subsequent CA signals; and
detecting an arrhythmia based on a presence or absence of one or more of the R-waves in at least a second segment of the CA signals;
wherein the CA sensing parameter defines a sensitivity profile and wherein the adjusting operation further comprises adjusting the CA sensing parameter to change a sensitivity of the sensitivity profile to at least reduce false arrhythmia detection due to undersensing or oversensing the R-waves;
wherein the detecting operation further comprises detecting the absence of the one or more of the R-waves in at least the second segment of the CA signals and based thereon declaring a brady pause-arrhythmia.

2. The method of claim 1, wherein the identifying, analyzing, adjusting and detecting operations are performed on at least one of: i) beat by beat, or ii) for ensembles of beats.

3. The method of claim 1, wherein the COI limit represents at least one of an expected variability of an amplitude of an R-wave or a presence of the R-wave.

4. The method of claim 1, wherein the motion data is indicative of the respiration cycle, the determining operation further comprises determining that the respiration cycle reduced an amplitude of the CA signals.

5. A computer implemented method, comprising:
under control of one or more processors of a medical device, where the one or more processors are configured with specific executable instructions,
obtaining motion data indicative of at least one of a posture or a respiration cycle;
obtaining cardiac activity (CA) signals for a series of beats;
identifying whether a characteristic of interest (COI) from at least a first segment of the CA signals exceeds a COI limit;
analyzing the motion data to determine whether at least one of the posture or the respiration cycle at least in part caused the COI to exceed the COI limit;
based on the analyzing operation, automatically adjusting a CA sensing parameter utilized by the medical device to detect R-waves in subsequent CA signals; and
detecting an arrhythmia based on a presence or absence of one or more of the R-waves in at least a second segment of the CA signals;

wherein the analyzing operation further comprises comparing the motion data to baseline motion data, wherein the baseline motion data is indicative of at least one of a supine baseline posture or a baseline respiration cycle, the comparing operation identifying motion changes that are associated with changes in an amplitude of the CA signals that occur with different postures and minute ventilation increase and decrease changes.

6. A computer implemented method, comprising:
under control of one or more processors of a medical device, where the one or more processors are configured with specific executable instructions,
obtaining motion data indicative of at least one of a posture or a respiration cycle;
obtaining cardiac activity (CA) signals for a series of beats;
identifying whether a characteristic of interest (COI) from at least a first segment of the CA signals exceeds a COI limit;
analyzing the motion data to determine whether at least one of the posture or the respiration cycle at least in part caused the COI to exceed the COI limit;
based on the analyzing operation, automatically adjusting a CA sensing parameter utilized by the medical device to detect R-waves in subsequent CA signals; and
detecting an arrhythmia based on a presence or absence of one or more of the R-waves in at least a second segment of the CA signals;
wherein the motion data is indicative of the posture, the determining operation further comprises determining that the motion data is indicative of a posture change that reduced an amplitude of the CA signals by an amount sufficient to cause the COI to exceed the COI limit.

7. The method of claim 6, wherein the determining operation further comprises determining that the posture change is a type of posture change that reduces an amplitude of the R-waves in the CA signals by an amount sufficient to prevent detection based on a sensing profile, wherein the CA sensing parameters are adjusted automatically to adjust the sensing profile.

8. A computer implemented method, comprising:
under control of one or more processors of a medical device, where the one or more processors are configured with specific executable instructions,
obtaining motion data indicative of at least one of a posture or a respiration cycle;
obtaining cardiac activity (CA) signals for a series of beats;
identifying whether a characteristic of interest (COI) from at least a first segment of the CA signals exceeds a COI limit;
analyzing the motion data to determine whether at least one of the posture or the respiration cycle at least in part caused the COI to exceed the COI limit;
based on the analyzing operation, automatically adjusting a CA sensing parameter utilized by the medical device to detect R-waves in subsequent CA signals;
detecting an arrhythmia based on a presence or absence of one or more of the R-waves in at least a second segment of the CA signals; and
comparing the subsequent CA signals to a current sensitivity level to determine whether the one or more of the R-waves are present within the subsequent CA signals.

9. The method of claim 8, further comprising repeating the comparing operation while progressively adjusting the current sensitivity level until i) the one or more R-waves are detected in a beat segment of interest in the CA signals and/or ii) the current sensitivity level reaches a sensitivity limit.

10. A system, comprising:
one or more processors of a medical device;
and a memory coupled to the one or more processors, wherein the memory stores program instructions, wherein the program instructions are executable by the one or more processors to:
obtain motion data indicative of at least one of a posture or a respiration cycle;
obtain cardiac activity (CA) signals for a series of beats;
identify whether a characteristic of interest (COI) from at least a first segment of the CA signals exceeds a COI limit;
analyze the motion data to determine whether at least one of the posture or the respiration cycle at least in part caused the COI to exceed the COI limit;
based on the analyze operation, automatically adjust a CA sensing parameter utilized by the medical device to detect R-waves in subsequent CA signals; and
detect an arrhythmia based on a presence or absence of one or more of the R-waves in at least a second segment of the CA signals;
wherein the CA sensing parameter defines a sensitivity profile and wherein the adjust includes adjust the CA sensing parameter to change a sensitivity of the sensitivity profile to at least reduce false arrhythmia detection due to undersensing or oversensing the R-waves;
wherein the detect includes detect the absence of the one or more of the R-waves in at least the second segment of the CA signals and based thereon declare a brady pause arrhythmia.

11. The system of claim 10, wherein the program instructions are further executable by the one or more processors to perform the identify, analyze, adjust and detect on at least one of: i) beat by beat, or ii) for ensembles of beats.

12. The system of claim 10, wherein the COI limit represents at least one of an expected variability of an amplitude of an R-wave or a presence of the R-wave.

13. The system of claim 10, wherein the motion data is indicative of the respiration cycle, the determine includes determine that the respiration cycle reduced an amplitude of the CA signals.

14. A system, comprising:
one or more processors of a medical device;
and a memory coupled to the one or more processors, wherein the memory stores program instructions, wherein the program instructions are executable by the one or more processors to:
obtain motion data indicative of at least one of a posture or a respiration cycle;
obtain cardiac activity (CA) signals for a series of beats;
identify whether a characteristic of interest (COI) from at least a first segment of the CA signals exceeds a COI limit;
analyze the motion data to determine whether at least one of the posture or the respiration cycle at least in part caused the COI to exceed the COI limit;
based on the analyze operation, automatically adjust a CA sensing parameter utilized by the medical device to detect R-waves in subsequent CA signals; and
detect an arrhythmia based on a presence or absence of one or more of the R-waves in at least a second segment of the CA signals;
wherein the analyze includes compare the motion data to baseline motion data, wherein the baseline motion data is indicative of at least one of a supine baseline posture or a baseline respiration cycle, the compare identifying motion changes that are associated with changes in an amplitude of the CA signals that occur with different postures and minute ventilation increase and decrease changes.

15. A system, comprising:
one or more processors of a medical device;
and a memory coupled to the one or more processors, wherein the memory stores program instructions, wherein the program instructions are executable by the one or more processors to:
obtain motion data indicative of at least one of a posture or a respiration cycle;
obtain cardiac activity (CA) signals for a series of beats;
identify whether a characteristic of interest (COI) from at least a first segment of the CA signals exceeds a COI limit;
analyze the motion data to determine whether at least one of the posture or the respiration cycle at least in part caused the COI to exceed the COI limit;
based on the analyze operation, automatically adjust a CA sensing parameter utilized by the medical device to detect R-waves in subsequent CA signals; and
detect an arrhythmia based on a presence or absence of one or more of the R-waves in at least a second segment of the CA signals;
wherein the motion data is indicative of the posture, the determine includes determine that the motion data is indicative of a posture change that reduced an amplitude of the CA signals by an amount sufficient to cause the COI to exceed the COI limit.

16. The system of claim 15, wherein the determine includes determine that the posture change is a type of posture change that reduces an amplitude of the R-waves in the CA signals by an amount sufficient to prevent detection based on a sensing profile and, wherein the program instructions are further executable by the one or more processors to automatically adjust the CA sensing parameters to adjust the sensing profile.

* * * * *